(12) United States Patent
Ly et al.

(10) Patent No.: US 7,750,014 B2
(45) Date of Patent: Jul. 6, 2010

(54) IMIDAZO[1,2-C]PYRIMIDINYLACETIC ACID DERIVATIVES

(75) Inventors: Tai-Wei Ly, San Diego, CA (US); Takashi Yoshino, Saitama (JP); Yuki Takekawa, Kyoto (JP); Takuya Shintani, Kyoto (JP); Hiromi Sugimoto, Kyoto (JP); Kevin Bacon, San Diego, CA (US); Klaus Urbahns, Lund (SE)

(73) Assignee: Actimis Pharmaceuticals, Inc., San Diego, CA (US)

( * ) Notice: Subject to any disclaimer, the term of this patent is extended or adjusted under 35 U.S.C. 154(b) by 1003 days.

(21) Appl. No.: 10/585,429

(22) PCT Filed: Jan. 19, 2005

(86) PCT No.: PCT/EP2005/000475

§ 371 (c)(1),
(2), (4) Date: Jul. 7, 2006

(87) PCT Pub. No.: WO2005/073234

PCT Pub. Date: Nov. 8, 2005

(65) Prior Publication Data

US 2009/0012102 A1    Jan. 8, 2009

(30) Foreign Application Priority Data

Jan. 31, 2004 (EP) .................................. 04002144

(51) Int. Cl.
*A01N 43/90* (2006.01)
*A61K 31/519* (2006.01)
*C07D 487/00* (2006.01)

(52) U.S. Cl. ..................................... 514/259.1; 544/281

(58) Field of Classification Search ........................ None
See application file for complete search history.

(56) References Cited

FOREIGN PATENT DOCUMENTS

| DE | 42 39 440 A | 6/1993 |
|----|-------------|--------|
| EP | 1 170 594 A | 1/2002 |
| EP | 1 413 306 A | 4/2004 |
| EP | 1471057 | 10/2004 |
| GB | 1356834 | 6/1974 |
| GB | 2 262 096 A | 6/2003 |
| WO | WO 01/83485 | 11/2001 |
| WO | WO 2004/058164 | 7/2004 |

OTHER PUBLICATIONS

Sugimoto, et al., J. Pharmacol Exp Ther 2003 305: 347-352.*
Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
"Burger's Medicinal Chemistry and Drug Discovery," 5th Ed. Part 1, pp. 975-977 (1995).*
Banker, et. al., Modern Pharmaceuticals, (1996) p. 596.*
Sugimoto et al., "An orally bioavailable small molecule antagonist of CRTH2, Ramatroban, inhibits prostaglandin D2-induced eosinophil migration in vitro", J Pharmacol and Exp Therapeutics 305(1):347-352 (2003).
Yamamoto et al., "The orally available spleen tyrosine kinase inhibitor 2-'7-(3,4-dimethoxyphenyl)-imidazo' 1,2-yrimidin-5-ylaminonicotinamide dihydrochloride blocks antigen-induced airway inflammation in rodents", J Pharmacol and Exp Therapeutics 306(3):1174-1181 (2003).
International Search Report of International Application No. PCT/EP2004/003910 having a Publication No. WO 04/096777.
Ly, T. W., et al, "Small-Molecule CRTH2 Antagonists for the Treatment of Allergic Inflammation: An Overview," *Expert Opin. Investig. Drugs*, 14(7): 769-773 (2005).
Ordukhanyan, A. A., et al, Khimiko-Farmatsevticheskii Zhurnal, 13(9): 36-40 (1979) (Article in Russian) provided).
Ordukhanyan, A. A., et al, Khimiko-Farmatsevticheskii Zhurnal, 13(9): 36-40 (1979) (English abstract).
Ulven, T., et al, "Novel Selective Orally Active CRTH2 Antagonists for Allergic Inflammation Developed from In Silico Derived Hits," *J. Med. Chem.*, 49:6638-6641 (2006).

* cited by examiner

*Primary Examiner*—James O Wilson
*Assistant Examiner*—Jeffrey H Murray
(74) *Attorney, Agent, or Firm*—Jones Day

(57) ABSTRACT

The present invention relates to an imidazo[1,2-c]pyrimidinylacetic acid derivative and salts thereof which is useful as an active ingredient of pharmaceutical preparations. The imidazo[1,2-c]pyrimidinylacetic acid derivative of the present invention has excellent CRTH2 (G-protein-coupled chemoattractant receptor, expressed on Th2 cells) antagonistic activity and can be used for the prophylaxis and treatment of diseases associated with CRTH2 activity, in particular for the treatment of allergic diseases, such as asthma, allergic rhinitis, atopic dermatitis, and allergic conjunctivitis; eosinophil-related diseases, such as Churg-Strauss syndrome and sinusitis; basophil-related diseases, such as basophilic leukemia, chronic urticaria and basophilic leukocytosis in human and other mammals; and inflammatory diseases characterized by T lymphocytes and profuse leukocyte infiltrates such as psoriasis, eczema, inflammatory bowel disease, ulcerative colitis, Crohn's disease, COPD (chronic obstructive pulmonary disorder) and arthritis.

13 Claims, No Drawings

IMIDAZO[1,2-C]PYRIMIDINYLACETIC ACID DERIVATIVES

This is a U.S. national stage application of the International Patent Application No. PCT/EP2005/000475, filed Jan. 19, 2005, which claims priority to European Patent Application No. 04002144.6, filed Jan. 31, 2004, all of which are incorporated herein by reference in their entirety.

DETAILED DESCRIPTION OF INVENTION

1. Technical Field

The present invention relates to a pyrimidinylacetic acid derivative which is useful as an active ingredient of pharmaceutical preparations. The pyrimidinylacetic acid derivative of the present invention has CRTH2 (G-protein-coupled chemoattractant receptor, expressed on Th2 cells) antagonistic activity and can be used for the prophylaxis and treatment of diseases associated with CRTH2 activity, in particular for the treatment of allergic diseases, such as asthma, allergic rhinitis, atopic dermatitis, and allergic conjunctivitis; eosinophil-related diseases, such as Churg-Strauss syndrome and sinusitis; basophil-related diseases, such as basophilic leukemia, chronic urticaria and basophilic leukocytosis in human and other mammals; and inflammatory diseases characterized by T lymphocytes and profuse leukocyte infiltrates such as psoriasis, eczema, inflammatory bowel disease, ulcerative colitis, Crohn's disease, COPD (chronic obstructive pulmonary disorder) and arthritis.

2. Background Art

CRTH2 is a G-protein-coupled chemoattractant receptor, expressed on Th2 cells (Nagata et al. J. Immunol., 162, 1278-1286, 1999), eosinophils and basophils (Hirai et al., J. Exp. Med., 193, 255-261, 2001).

Th2-polarization has been seen in allergic diseases, such as asthma, allergic rhinitis, atopic dermatitis and allergic conjunctivitis (Romagnani S. Immunology Today, 18, 263-266, 1997; Hammad H. et al., Blood, 98, 1135-1141, 2001). Th2 cells regulate allergic diseases by producing Th2 cytokines, such as IL-4, IL-5 and IL-13 (Oriss et al., J. Immunol., 162, 1999-2007, 1999; Viola et al., Blood, 91, 2223-2230, 1998; Webb et al., J. Immunol., 165, 108-113, 2000; Dumont F. J., Exp. Opin. Ther. Pat., 12, 341-367, 2002). These Th2 cytokines directly or indirectly induce migration, activation, priming and prolonged survival of effector cells, such as eosinophils and basophils, in allergic diseases (Sanz et al., J. Immunol., 160, 5637-5645, 1998; Pope et al., J. Allergy Clin. Immunol., 108, 594-601, 2001; Teran L. M., Clin. Exp. Allergy, 29, 287-290, 1999).

PGD$_2$, a ligand for CRTH2, is produced from mast cells and other important effector cells in allergic diseases (Nagata et al., FEBS Lett. 459, 195-199, 1999; Hirai et al., J. Exp. Med., 193, 255-261, 2001). PGD$_2$ induces migration and activation of Th2 cells, eosinophils, and basophils, in human cells via CRTH2 (Hirai et al., J. Exp. Med., 193, 255-261, 2001; Gervais et al., J. Allergy Clin. Immunol., 108, 982-988, 2001; Sugimoto et al., J. Pharmacol. Exp. Ther., 305, (1), 347-52, 2003).

Therefore, antagonists which inhibit the binding of CRTH2 and PGD$_2$ should be useful for the treatment of allergic diseases, such as asthma, allergic rhinitis, atopic dermatitis and allergic conjunctivitis.

In addition, several lines of experimental evidence have demonstrated the contribution of eosinophils in sinusitis (Hamilos et al., Am. J. Respir. Cell and Mol. Biol., 15, 443-450, 1996; Fan et al., J. Allergy Clin. Immunol., 106, 551-558, 2000), and Churg-Strauss syndrome (Coffin et al., J. Allergy Clin. Immunol., 101, 116-123, 1998; Kurosawa et al., Allergy, 55, 785-787, 2000). In the tissues of these patients, mast cells can be observed to be colocalized with eosinophils (Khan et al., J. Allergy Clin. Immunol., 106, 1096-1101, 2000). It is suggested that PGD$_2$ production from mast cells induces the recruitment of eosinophils. Therefore, CRTH2 antagonists are also useful for the treatment of other eosinophil-related diseases such as Churg-Strauss syndrome and sinusitis. CRTH2 antagonists can also be useful for the treatment of some basophil-related diseases such as basophilic leukemia, chronic urticaria and basophilic leukocytosis, because of high expression of CRTH2 on basophils.

A. F. Kluge discloses the synthesis of imidazo[1,2-c]pyrimidine analog represented by the general formula:

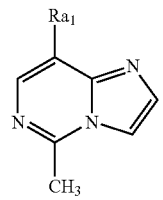

wherein Ra$_1$ represents

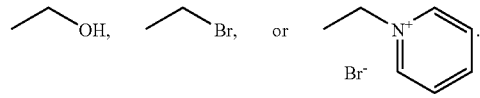

(Journal of Heterocyclic Chemistry (1978), 15(1), 119-21).

However, there is no disclosure of imidazo[1,2-c]pyrimidinylacetic acid derivatives having CRTH2 antagonistic activity.

The development of a compound, which has effective CRTH2 antagonistic activity and can be used for the prophylaxis and treatment of diseases associated with CRTH2 activity, has been desired.

SUMMARY OF THE INVENTION

This invention is to provide an imidazo[1,2-c]pyrimidinylacetic acid derivative of the formula (I), their tautomeric and stereoisomeric form, and salts thereof:

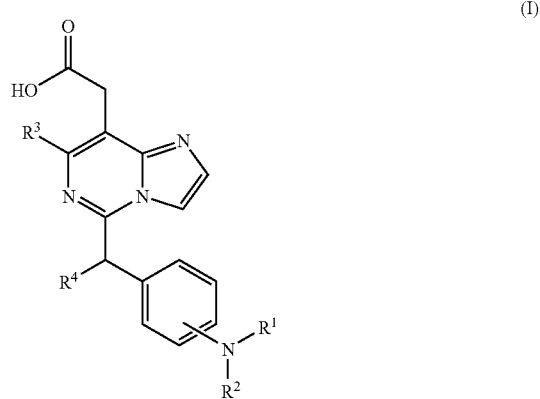

wherein
R$^1$ represents

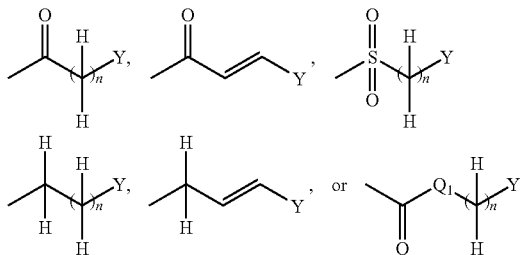

in which
n represents an integer of 0 to 6;
Q$_1$ represents —NH—, —N(C$_{1-6}$alkyl)-, or —O—;
Y represents hydrogen, C$_{3-8}$ cycloalkyl optionally substituted by C$_{1-6}$ alkyl, C$_{3-8}$ cycloalkyl fused by benzene, aryl or heteroaryl, wherein said aryl and heteroaryl are optionally substituted at a substitutable position with one or more substituents selected from the group consisting of cyano, halogen, nitro, guanidino, pyrrolyl, sulfamoyl, C$_{1-6}$ alkylaminosulfonyl, di(C$_{1-6}$ alkyl)aminosulfonyl, phenyloxy, phenyl, amino, C$_{1-6}$alkylamino, di-(C$_{1-6}$alkyl)amino, C$_{1-6}$ alkoxycarbonyl, C$_{1-6}$ alkanoyl, C$_{1-6}$ alkanoylamino, carbamoyl, C$_{1-6}$alkylcarbamoyl, di-(C$_{1-6}$alkyl)carbamoyl, C$_{1-6}$ alkylsulfonyl, C$_{1-6}$alkyl optionally substituted by mono-, di-, or tri-halogen, C$_{1-6}$ alkoxy optionally substituted by mono-, di-, or tri-halogen and C$_{1-6}$ alkylthio optionally substituted by mono-, di-, or tri-halogen, or aryl fused by 1,3-dioxolane;
R$^2$ represents hydrogen or C$_{1-6}$ alkyl;
R$^3$ represents hydrogen, halogen, C$_{1-6}$ alkyl optionally substituted by mono-, di-, or tri-halogen, C$_{1-6}$ alkoxy optionally substituted by mono-, di-, or tri-halogen,

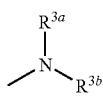

in which
R$^{3a}$ and R$^{3b}$ independently represent C$_{3-8}$ cycloalkyl, or C$_{1-6}$ alkyl optionally substituted by carboxy, C$_{3-8}$ cycloalkyl, carbamoyl, C$_{1-6}$ alkylcarbamoyl, aryl-substituted C$_{1-6}$ alkylcarbamoyl, C$_{1-6}$ alkylcarbamoyl, di(C$_{1-6}$alkyl)-carbamoyl, C$_{3-8}$ cycloalkylcarbamoyl, C$_{3-8}$heterocyclocarbonyl, C$_{1-6}$alkyl-amino, di(C$_{1-6}$alkyl)amino or C$_{1-6}$ alkoxy,

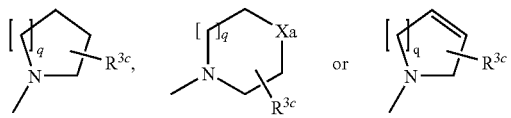

in which
q represents an integer of 1 to 3;
R$^{3c}$ represents hydrogen, hydroxy, carboxy, or C$_{1-6}$ alkyl optionally substituted by hydroxy, carboxy or (phenyl-substituted C$_{1-6}$ alkyl)-carbamoyl;
Xa represents —O—, —S— or —N(R$^{3d}$)— in which
R$^{3d}$ represents hydrogen or C$_{1-6}$ alkyl; and
R$^4$ represents hydrogen or C$_{1-6}$ alkyl.
In one embodiment, compounds of the formula (I) are those wherein:
R$^1$ represents

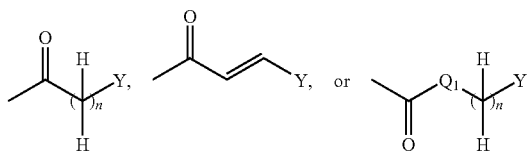

in which
n represents an integer of 0 to 2;
Q$_1$ represents —NH—, —N(C$_{1-6}$alkyl)-, or —O—;
Y represents C$_{3-8}$ cycloalkyl optionally substituted by C$_{1-6}$ alkyl, C$_{3-8}$ cyclo-alkyl fused by benzene, aryl selected from the group consisting of phenyl and naphthyl, or heteroaryl selected from the group consisting of indolyl, quinolyl, benzofuranyl, furanyl and pyridyl, wherein said aryl and hetero-aryl are optionally substituted at a substitutable position with one or more substituents selected from the group consisting of cyano, halogen, nitro, pyrrolyl, sulfamoyl, C$_{1-6}$ alkylaminosulfonyl, di(C$_{1-6}$ alkyl)aminosulfonyl, phenyloxy, phenyl, C$_{1-6}$alkylamino, di(C$_{1-6}$alkyl) amino, C$_{1-6}$ alkoxy-carbonyl, C$_{1-6}$ alkanoylamino, carbamoyl, C$_{1-6}$ alkylcarbamoyl, di-(C$_{1-6}$ alkyl)carbamoyl, C$_{1-6}$ alkylsulfonyl, C$_{1-6}$alkyl optionally substituted by mono-, di-, or tri-halogen, C$_{1-6}$ alkoxy optionally substituted by mono-, di-, or tri-halogen and C$_{1-6}$ alkylthio optionally substituted by mono-, di-, or tri-halogen; and
R$^2$ represents hydrogen.
In another embodiment, compounds of the formula (I) are those wherein:
R$^3$ represents hydrogen, halogen, C$_{1-6}$ alkyl optionally substituted by mono-, di-, or tri-halogen, C$_{1-6}$ alkoxy optionally substituted by mono-, di-, or tri-halogen,

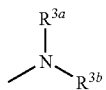

in which
R$^{3a}$ and R$^{3b}$ independently represent C$_{1-6}$ alkyl optionally substituted by carboxy, C$_{3-8}$ cycloalkyl, carbamoyl, C$_{1-6}$ alkylcarbamoyl, di(C$_{1-6}$ alkyl)carbamoyl, C$_{3-8}$ cycloalkylcarbamoyl, C$_{3-8}$ heterocyclo-carbonyl, C$_{1-6}$alkylamino, di(C$_{1-6}$alkyl)amino or C$_{1-6}$ alkoxy,

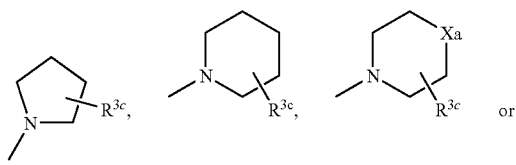

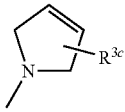

in which
R³ᶜ represents hydrogen, hydroxy, carboxy, or C₁₋₆ alkyl optionally substituted by hydroxy, carboxy or (phenyl-substituted C₁₋₆ alkyl)-carbamoyl;
Xa represents —O—, —S— or —N(R³ᵈ)—,
in which
R³ᵈ represents C₁₋₆ alkyl.

In another embodiment, compounds of the formula (I-i) are

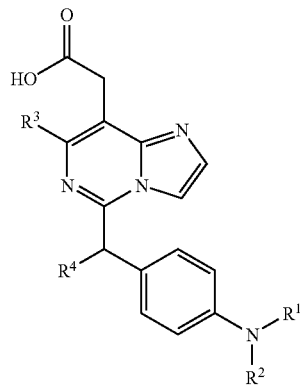

(I-i)

wherein
R¹ represents

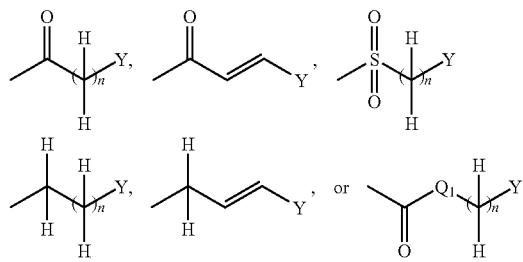

in which
n represents an integer of 0 to 2;
Q₁ represents —NH—, —N(C₁₋₆ alkyl)-, or —O—;
Y represents phenyl, naphthyl, indolyl, quinolyl, benzofuranyl, furanyl or pyridyl,
wherein said phenyl, naphthyl, indolyl, quinolyl, benzofuranyl, furanyl and pyridyl are optionally substituted at a substitutable position with one or two substituents selected from the group consisting of cyano, halogen, nitro, phenyloxy, phenyl, C₁₋₆alkyl optionally substituted by mono-, di-, or tri-halogen, C₁₋₆ alkoxy optionally substituted by mono-, di-, or tri-halogen and C₁₋₆ alkylthio optionally substituted by mono-, di-, or tri-halogen;
R² represents hydrogen or C₁₋₆ alkyl;
R³ represents hydrogen, halogen, C₁₋₆ alkyl optionally substituted by mono-, di-, or tri-halogen, C₁₋₆ alkoxy,

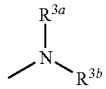

in which
R³ᵃ and R³ᵇ independently represent C₃₋₈ cycloalkyl, or C₁₋₆ alkyl optionally substituted by C₃₋₈ cycloalkyl, carbamoyl, C₁₋₆ alkylcarbamoyl, phenyl-substituted C₁₋₆ alkylcarbamoyl, C₁₋₆ alkylcarbamoyl, di(C₁₋₆ alkyl)-carbamoyl, C₃₋₈ cycloalkylcarbamoyl, C₃₋₈heterocyclocarbonyl, C₁₋₆alkyl-amino, di(C₁₋₆alkyl)amino or C₁₋₆ alkoxy,

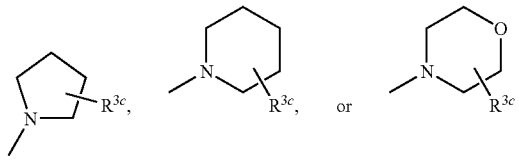

R³ᶜ represents hydrogen, hydroxy, carboxy, or C₁₋₆ alkyl optionally substituted by hydroxy, carboxy or (phenyl-substituted C₁₋₆ alkyl)carbamoyl; and
R⁴ represents hydrogen, or methyl.

Preferred are compounds of the formula (I) in which R² represents hydrogen.

Preferred are compounds of the formula (I) in which R³ represents hydrogen and halogen preferably chlorine.

Preferred are compounds of the formula (I) in which R⁴ represents hydrogen.

Preferred are compounds of the formula (I) in which R¹ represents one of the groups

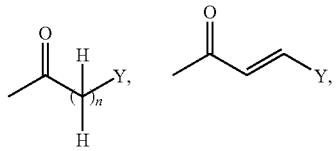

The preferable compounds of the present invention are as follows:

[7-chloro-5-(4-{[4-(trifluoromethyl)benzoyl]amino}benzyl)imidazo[1,2-c]pyrimidin-8-yl]acetic acid;

(7-chloro-5-{4-[(3,4-dichlorobenzoyl)amino]benzyl}imidazo[1,2-c]pyrimidin-8-yl)acetic acid;

{7-chloro-5-[4-(2-naphthoylamino)benzyl]imidazo[1,2-c]pyrimidin-8-yl}acetic acid;

[7-chloro-5-{4-[[(2E)-3-phenylprop-2-enoyl]amino}benzyl)imidazo[1,2-c]pyrimidin-8-yl]acetic acid;

[7-chloro-5-(4-{[(2E)-3-(4-chlorophenyl)prop-2-enoyl]amino}benzyl)imidazo[1,2-c]pyrimidin-8-yl]acetic acid;

(5-{4-[(3,4-dichlorobenzoyl)amino]benzyl}imidazo[1,2-c]pyrimidin-8-yl)acetic acid;

[5-(4-{[4-(trifluoromethyl)benzoyl]amino}benzyl)imidazo[1,2-c]pyrimidin-8-yl]acetic acid.

and their tautomeric and stereoisomeric form, and salts thereof.

The imidazo[1,2-c]pyrimidinylacetic acid derivative of the formula (I) shows excellent CRTH2 antagonistic activity.

They are, therefore, suitable especially for the prophylaxis and treatment of diseases associated with CRTH2 activity.

More specifically, the imidazo[1,2-c]pyrimidinylacetic acid derivative of the formula (I) and (I-i) are effective for the treatment or prevention of allergic diseases such as asthma, allergic rhinitis, atopic dermatitis and allergic conjunctivitis.

Compounds of the formula (I) and (I-i) are also useful for the treatment or prevention of diseases such as Churg-Strauss syndrome, sinusitis, basophilic leukemia, chronic urticaria and basophilic leukocytosis, since such diseases are also related to CRTH2 activity.

Further, the present invention provides a medicament, which includes one of the compounds, described above and optionally pharmaceutically acceptable excipients.

Alkyl per se and "alk" and "alkyl" in alkoxy, alkanoyl, alkylamino, alkylaminocarbonyl, alkyl-aminosulphonyl, alkylsulphonylamino, alkoxycarbonyl, alkoxycarbonylamino and alkanoylamino represent a linear or branched alkyl radical having generally 1 to 6, preferably 1 to 4 and particularly preferably 1 to 3 carbon atoms, representing illustratively and preferably methyl, ethyl, n-propyl, isopropyl, tert-butyl, n-pentyl and n-hexyl.

Alkoxy illustratively and preferably represents methoxy, ethoxy, n-propoxy, isopropoxy, tert-butoxy, n-pentoxy and n-hexoxy.

Alkanoyl illustratively and preferably represents acetyl and propanoyl.

Alkylamino represents an alkylamino radical having one or two (independently selected) alkyl substituents, illustratively and preferably representing methylamino, ethylamino, n-propylamino, isopropylamino, tert-butylamino, n-pentylamino, n-hexyl-amino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Alkylaminocarbonyl or alkylcarbamoyl represents an alkylaminocarbonyl radical having one or two (independently selected) alkyl substituents, illustratively and preferably representing methyl-aminocarbonyl, ethylaminocarbonyl, n-propylaminocarbonyl, isopropylamino-carbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentyl-amino-carbonyl and N-n-hexyl-N-methylaminocarbonyl.

Alkylaminosulphonyl represents an alkylaminosulphonyl radical having one or two (independently selected) alkyl substituents, illustratively and preferably representing methylaminosulphonyl, ethylaminosulphonyl, n-propylaminosulphonyl, isopropylaminosulphonyl, tert-butylaminosulphonyl, n-pentylaminosulphonyl, n-hexyl-aminosulphonyl, N,N-dimethylaminosulphonyl, N,N-diethylaminosulphonyl, N-ethyl-N-methylamino-sulphonyl, N-methyl-N-n-propylaminosulphonyl, N-isopropyl-N-n-propylaminosulphonyl, N-t-butyl-N-methylaminosulphonyl, N-ethyl-N-n-pentyl-aminosulphonyl and N-n-hexyl-N-methylaminosulphonyl.

Alkylsulphonylamino illustratively and preferably represents methylsulphonylamino, ethyl-sulphonylamino, n-propylsulphonylamino, isopropylsulphonylamino, tert-butylsulphonylamino, n-pentylsulphonylamino and n-hexylsulphonylamino.

Alkoxycarbonyl illustratively and preferably represents methoxycarbonyl, ethoxycarbonyl, n-prop-oxycarbonyl, isopropoxycarbonyl, tert-butoxycarbonyl, n-pentoxycarbonyl and n-hexoxycarbonyl. Alkoxycarbonylamino illustratively and preferably represents methoxycarbonylamino, ethoxycarbonylamino, n-propoxycarbonylamino, isopropoxycarbonylamino, tert-butoxycarbonylamino, n-pentoxycarbonylamino and n-hexoxycarbonylamino.

Alkanoylamino illustratively and preferably represents acetylamino and ethylcarbonylamino.

Cycloalkyl per se and in cycloalkylamino and in cycloalkylcarbonyl represents a cycloalkyl group having generally 3 to 8 and preferably 5 to 7 carbon atoms, illustratively and preferably representing cyclopropyl, cyclobutyl, cyclopentyl, cyclohexyl and cycloheptyl.

Cycloalkylamino represents a cycloalkylamino radical having one or two (independently selected) cycloalkyl substituents, illustratively and preferably representing cyclopropylamino, cyclobutyl-amino, cyclopentylamino, cyclohexylamino and cycloheptylamino.

Cycloalkylcarbonyl illustratively and preferably represents cyclopropylcarbonyl, cyclobutyl-carbonyl, cyclopentylcarbonyl, cyclohexylcarbonyl and cycloheptylcarbonyl.

Aryl per se and in arylamino and in arylcarbonyl represents a mono- to tricyclic aromatic carbocyclic radical having generally 6 to 14 carbon atoms, illustratively and preferably representing phenyl, naphthyl and phenanthrenyl.

Arylamino represents an arylamino radical having one or two (independently selected) aryl substituents, illustratively and preferably representing phenylamino, diphenylamino and naphthyl-amino.

Arylcarbonyl illustratively and preferably represents phenylcarbonyl and naphthylcarbonyl.

Heteroaryl per se and in heteroarylamino and heteroarylcarbonyl represents an aromatic mono- or bicyclic radical having generally 5 to 10 and preferably 5 or 6 ring atoms and up to 5 and preferably up to 4 hetero atoms selected from the group consisting of S, O and N, illustratively and preferably representing thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

Heteroarylamino represents an heteroarylamino radical having one or two (independently selected) heteroaryl substituents, illustratively and preferably representing thienylamino, furylamino, pyrrolylamino, thiazolylamino, oxazolylamino, imidazolyl-amino, pyridylamino, pyrimidylamino, pyridazinylamino, indolylamino, indazolylamino, benzofuranylamino, benzothiophenylamino, quinolinylamino, isoquinolinylamino.

Heteroarylcarbonyl illustratively and preferably represents thienylcarbonyl, furylcarbonyl, pyrrolylcarbonyl, thiazolylcarbonyl, oxazolylcarbonyl, imidazolyl-carbonyl, pyridylcarbonyl, pyrimidylcarbonyl, pyridazinylcarbonyl, indolylcarbonyl, indazolylcarbonyl, benzofuranylcarbonyl, benzothiophenylcarbonyl, quinolinyl-carbonyl, isoquinolinylcarbonyl.

Heterocyclyl per se and in heterocyclylcarbonyl represents a mono- or polycyclic, preferably mono- or bicyclic, nonaromatic heterocyclic radical having generally 4 to 10 and preferably 5 to 8 ring atoms and up to 3 and preferably up to 2 hetero atoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two hetero atoms selected from the group consisting of O, N and S, such as illustratively and preferably tetrahydrofuran-2-yl, pyrrolidin-2-yl, pyrrolidin-3-yl, pyrrolinyl, piperidinyl, morpholinyl, perhydroazepinyl.

Heterocyclylcarbonyl illustratively and preferably represents tetrahydrofuran-2-carbonyl, pyrrolidine-2-carbonyl, pyrrolidine-3-carbonyl, pyrrolinecarbonyl, piperidinecarbonyl, morpho-linecarbonyl, perhydroazepinecarbonyl.

EMBODIMENT OF THE INVENTION

Compounds of the formula (I) of the present invention can be, but not limited to be, prepared by combining various known methods. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis (3rd Edition)" by Greene and Wuts, John Wiley and Sons, New York 1999.

Compounds of the formula (I) of the present invention can be, but not limited to be, prepared by the Method [A], [B] [C], [D], [E], [F], [G], [H] or [I] below.

[Method A]

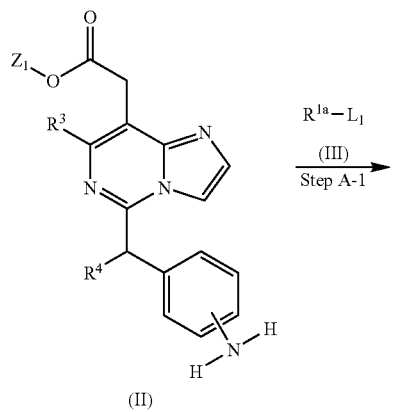

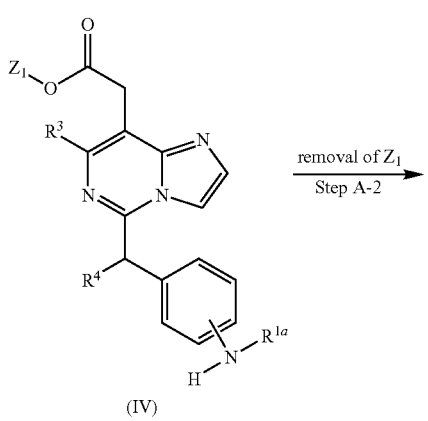

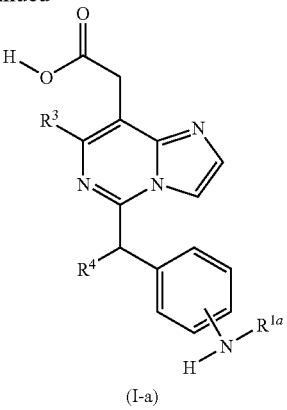

(I-a)

Compounds of the formula (I-a) (wherein $R^3$ and $R^4$ are the same as defined above and $R^{1a}$ is

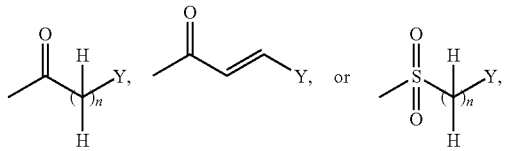

in which n and Y are the same as defined above) can be, for instance, prepared by the following procedures in two steps.

In Step A-1, compounds of the formula (IV) (wherein $R^{1a}$, $R^3$ and $R^4$ are the same as defined above and $Z_1$ is $C_{1-6}$ alkyl, benzyl, 4-methoxybenzyl or 3,4-dimethoxybenzyl) can be prepared by the reaction of compounds of the formula (II) (wherein $R^3$, $R^4$ and $Z_1$ are the same as defined above) with compounds of the formula (III) (wherein $R^{1a}$ is the same as defined above and $L_1$ represents a leaving group including, for instance, halogen atom such as chlorine, bromine and iodine atom, azole such as imidazole and triazole, and hydroxy)

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydro-carbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

The reaction can be advantageously conducted in the presence of a base including, for instance, sodium carbonate, potassium carbonate, pyridine, triethylamine and N,N-diisopropylethylamine, dimethylaniline, diethylaniline, and others.

In the case $L_1$ in compounds of the formula (III) (wherein $R^{1a}$ is

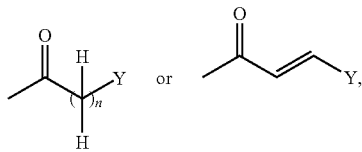

in which n and Y are the same as defined above) represents hydroxy, compounds of the formula (IV) (wherein $R^3$, $R^4$ and $Z_1$ are the same as defined above and $R^{1a}$ is

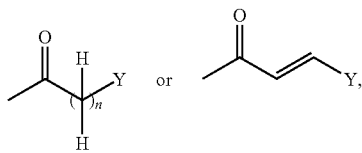

in which n and Y are the same as defined above) can be prepared by the reaction of compounds of the formula (II) (wherein $R^3$, $R^4$ and $Z_1$ are the same as defined above) with compounds of the formula (III) using a coupling agent including, for instance, carbodiimides such as N,N-dicyclo-hexyl-carbodiimide and 1-(3-dimethylaminopropyl)-3-ethylcarbodiimide, benzotriazole-1-yl-oxy-tris-pyrrolidino-phosphonium hexafluorophosphate (PyBOP), diphenylphosphoryl azide. N-hydroxysuccinimide, 1-hydroxybenzothiazole monohydrate (HOBt), and the like can be used as an accelerator of the reaction.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydro-carbons such as benzene, toluene and xylene; nitrites such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

In Step A-2, compounds of the formula (I-a) (wherein $R^{1a}$, $R^3$ and $R^4$ are the same as defined above) can be prepared by the removal of protective group $Z_1$ of compounds of the formula (IV) (wherein $R^{1a}$, $R^3$, $R^4$ and $Z_1$ are the same as defined above).

The removal of protective group $Z_1$ can be conducted by using a base including, for instance, sodium hydroxide, lithium hydroxide and potassium hydroxide, or an acid including, for instance, HCl, HBr, trifluoroacetic acid and $BBr_3$. The deprotection can also be done by hydrogenation using a catalyst including, for instance, palladium on carbon and palladium hydroxide, when $Z_1$ is benzyl, 4-methoxybenzyl or 3,4-dimethoxybenzyl. Also, the deprotection can be done by using a reagent such as ceric ammonium nitrate (CAN) or 2,3-dichloro-5,6-dicyano-1,4-benzoquinone (DDQ), when $Z_1$ is 4-methoxybenzyl or 3,4-dimethoxybenzyl.

The reaction can be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), sulfoxides such as dimethylsulfoxide (DMSO), alcohols such as methanol, ethanol, 1-propanol, isopropanol and tert-butanol, water and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

Compounds of the formula (III) are commercially available or can be synthesized by conventional methods.

[Method B]

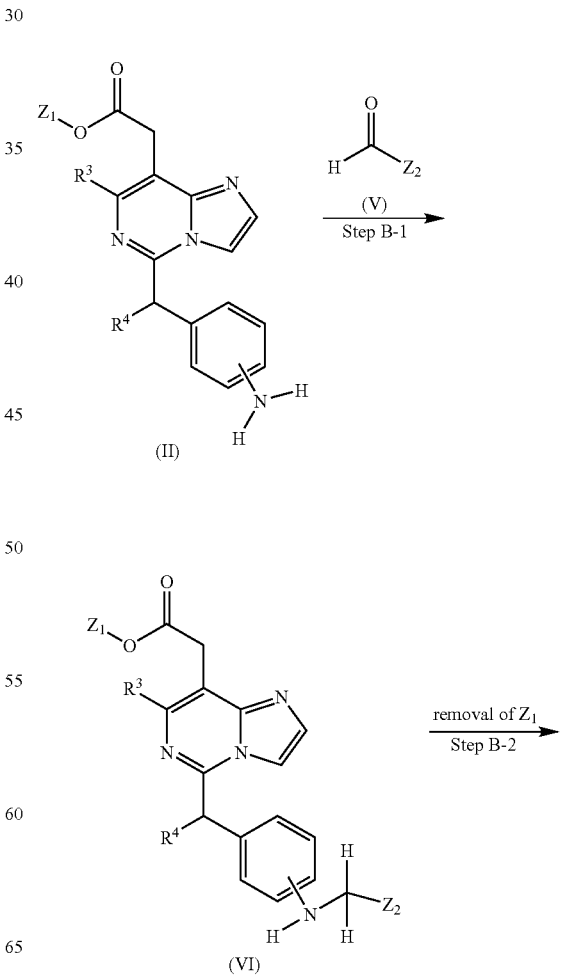

[Method C]

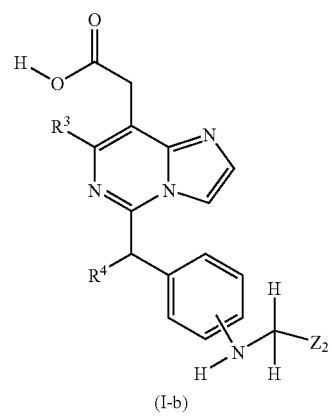

(I-b)

Compounds of the formula (I-b) (wherein $R^3$ and $R^4$ are the same as defined above and $Z_2$ is

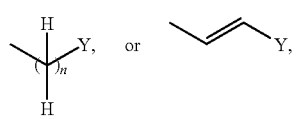

in which n and Y are the same as defined above) can be, for instance, prepared by the following procedures in two steps.

In Step B-1, compounds of the formula (VI) (wherein $R^3$, $R^4$, $Z_1$ and $Z_2$ are the same as defined above) can be prepared by the reaction of compounds of the formula (II) (wherein, $R^3$, $R^4$ and $Z_1$ are the same as defined above) with compounds of the formula (V) (wherein $Z_2$ is the same as defined above) using a reducing agent such as sodium triacetoxyborohydride.

The reaction can be advantageously conducted in the presence of an acid such as acetic acid or hydrochloric acid, or a dehydrating agent such as molecular sieves.

The reaction may be carried out in a solvent including, for instance, halogenated hydrocarbons such as 1,2-dichloroethane, ethers such as diethyl ether, isopropyl ether, dioxane and tetra-hydrofuran (THF) and 1,2-dimethoxyethane; aromatic hydrocarbons such as benzene, toluene and xylene, and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

In Step B-2, compounds of the formula (I-b) (wherein $R^3$, $R^4$ and $Z_2$ are the same as defined above) can be prepared by the removal of protective group $Z_1$ of compounds of the formula (VI) (wherein $R^3$, $R^4$, $Z_1$ and $Z_2$ are the same as defined above) in a similar manner of Step A-2 for the preparation of compounds of the formula (I-a).

Compounds of the formula (V) are commercially available or can be synthesized by conventional methods.

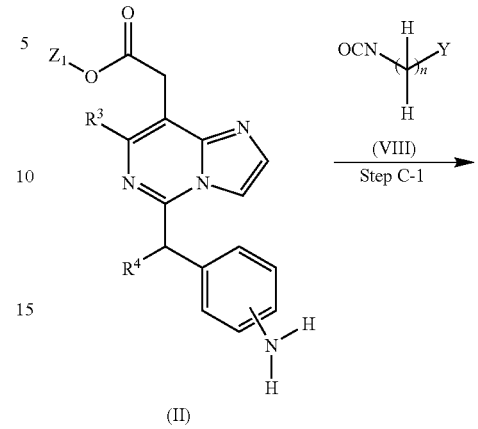

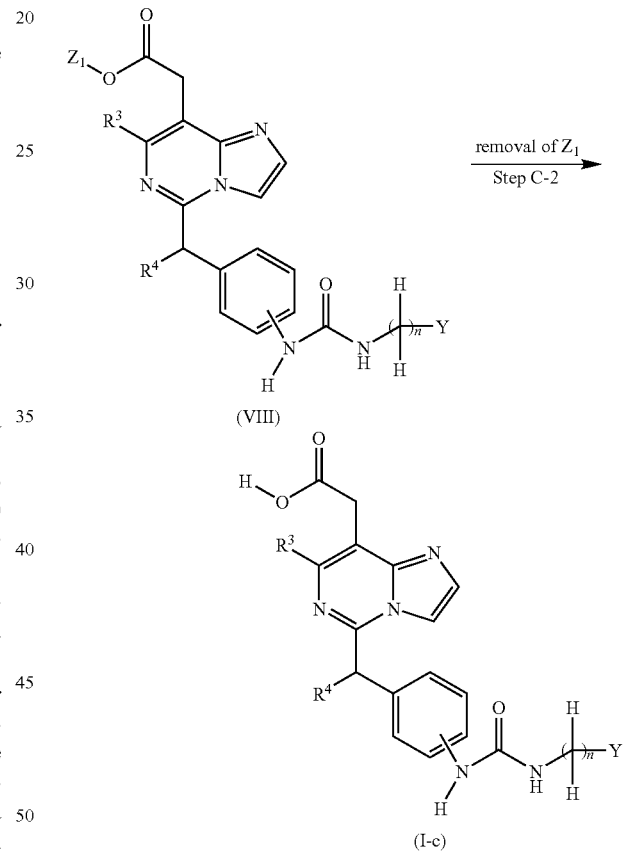

Compounds of the formula (Is) (wherein n, $R^3$, $R^4$ and Y are the same as defined above) can be, for instance, prepared by the following procedures in two steps.

In Step C-1, Compounds of the formula (VIII) (wherein n, $R^3$, $R^4$, Y and $Z_1$ are the same as defined above) can be prepared by the reaction of compounds of the formula (II) (wherein $R^3$, $R^4$ and $Z_1$ are the same as defined above) with compounds of the formula (VII) (wherein n and Y are the same as defined above)

The reaction may be carried out in a solvent including, for instance, halogenated hydrocarbons such as dichloromethane, chloroform and 1,2-dichloroethane; ethers such as diethyl ether, iso-propyl ether, dioxane and tetrahydrofuran (Th) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

In Step C-2, compounds of the formula (I-c) (wherein n, $R^3$, $R^4$ and Y are the same as defined above) can be prepared by the removal of protective group $Z_1$ of compounds of the formula (VIII) (wherein n, $R^3$, $R^4$, Y and $Z_1$ are the same as defined above) in a similar manner of Step A-2 for the preparation of compounds of the formula (I-a).

Compounds of the formula (VII) are commercially available or can be synthesized by conventional methods.

[Method D]

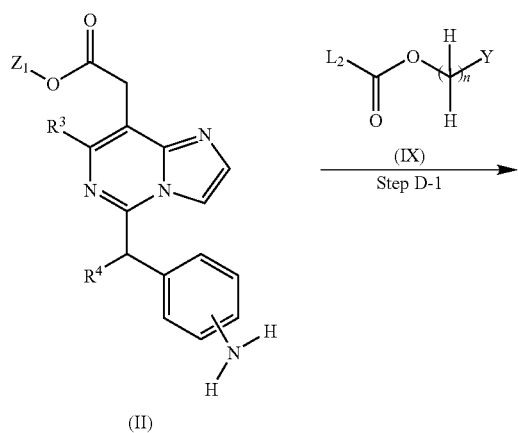

(II)

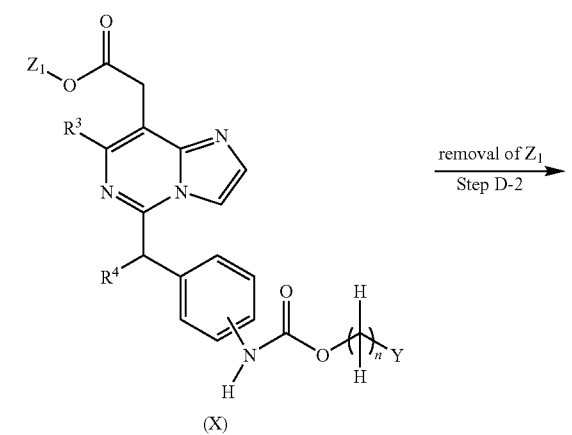

(X)

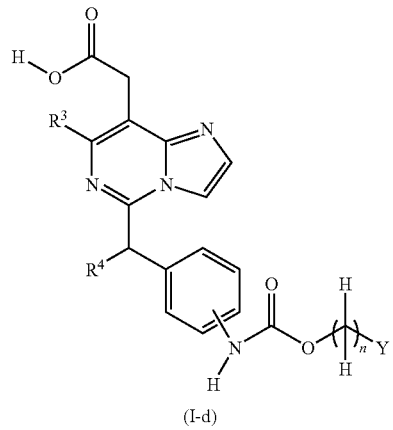

(I-d)

Compounds of the formula (I-d) (wherein n, $R^3$, $R^4$ and Y are the same as defined above) can be, for instance, prepared by the following procedures in two steps.

In Step D-1, Compounds of the formula (X) (wherein n, $R^3$, $R^4$, Y and $Z_1$ are the same as defined above) can be prepared by the reaction of compounds of the formula (II) (wherein $R^3$, $R^4$ and $Z_1$ are the same as defined above) with compounds of the formula (IX) (wherein n and Y are the same as defined above and $L_2$ represents a leaving group including, for instance, halogen atom such as chlorine and bromine)

The reaction may be carried out in a solvent including, for instance, halogenated hydrocarbons such as dichloromethane, chloroform and 1,2-dichloroethane; ethers such as diethyl ether, iso-propyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

In Step C-2, compounds of the formula (I-d) (wherein n, $R^3$, $R^4$ and Y are the same as defined above) can be prepared by the removal of protective group $Z_1$ of compounds of the formula (VIII) (wherein n, $R^3$, $R^4$, Y and $Z_1$ are the same as defined above) in a similar manner of Step A-2 for the preparation of compounds of the formula (I-a).

Compounds of the formula (IX) are commercially available or can be synthesized by conventional methods.

[Method E]

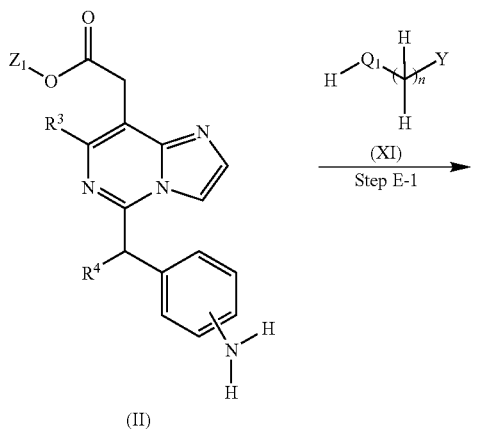

Compounds of the formula (I-e) (wherein n, $R^3$, $R^4$ and Y are the same as defined above and $Q_1$ represents —NH—, —N($C_{1-6}$ alkyl)-, or —O—) can be, for instance, prepared by the following procedures in two steps.

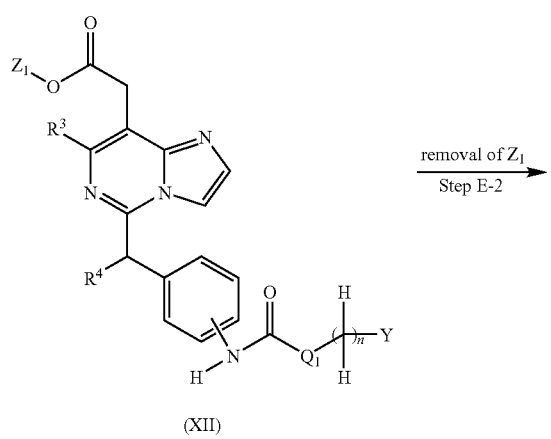

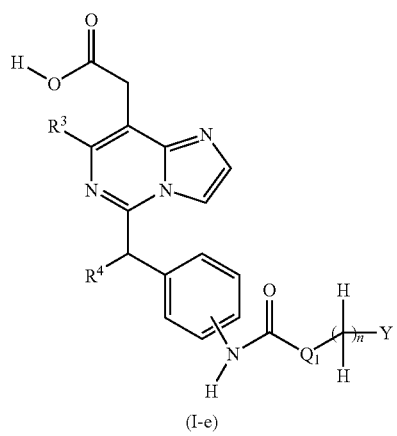

In Step E-1, Compounds of the formula (XII) (wherein n, $Q_1$, $R^3$, $R^4$, Y and $Z_1$ are the same as defined above) can be prepared by the reaction of compounds of the formula (II) (wherein $R^3$, $R^4$ and $Z_1$ are the same as defined above), compounds of the formula (XI) (wherein n, $Q_1$ and Y are the same as defined above) and agent including, for instance, aryl formate derivative such as phenyl chloroformate; halocarbonyl derivative such as phosgene, diphosgene, and triphosgene; carbonyldiazole derivative such as 1,1-carbonyldiimidazole (CDI), and 1,1'-carbonyldi(1,2,4-triazole) (CDT), and the like.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydro-carbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

The reaction can be advantageously carried out in the presence of a base including, for instance, organic amines such as pyridine, triethylamine and N,N-diisopropylethylamine, dimethylaniline, diethylaniline, 4-dimethylaminopyridine, and others.

In Step E-2, compounds of the formula (I-e) (wherein n, $Q_1$, $R^3$, $R^4$ and Y are the same as defined above) can be prepared by the removal of protective group $Z_1$ of compounds of the formula (XII) (wherein n, $Q_1$, $R^3$, $R^4$, Y and $Z_1$ are the same as defined above) in a similar manner of Step A-2 for the preparation of compounds of the formula (I-a).

Compounds of the formula (XI) are commercially available or can be synthesized by conventional methods.

[Method F]

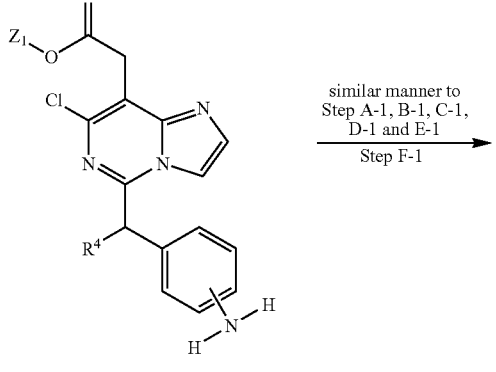

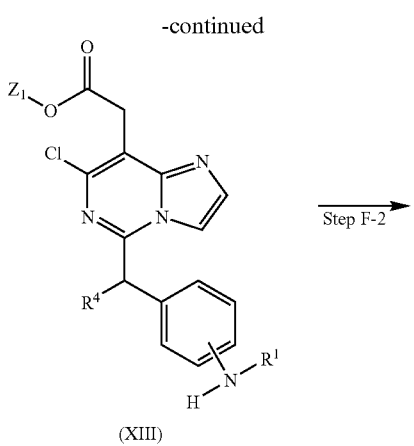
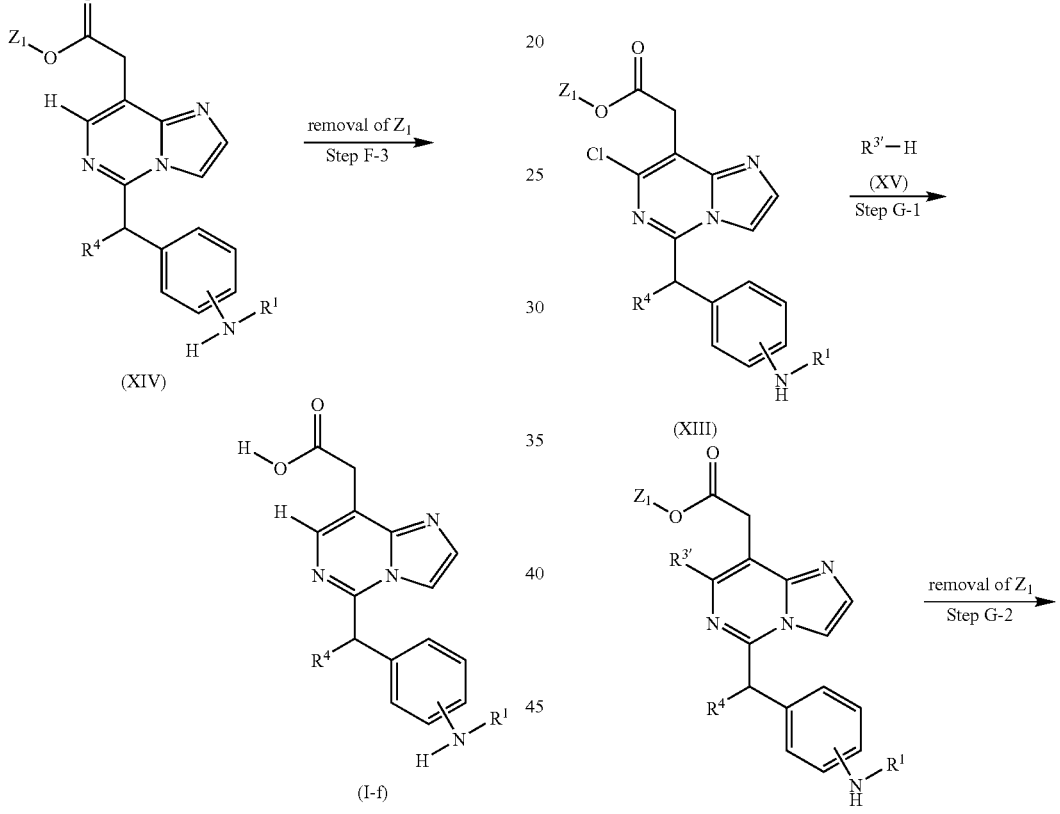

Compounds of the formula (I-f) (wherein $R^1$ and $R^4$ are the same as defined above), can be prepared by the following procedures.

In Step F-1, compounds of the formula (XIII) (wherein $R^1$, $R^4$ and $Z_1$ are the same as defined above) can be prepared by the reaction of compounds of the formula (II-a) (wherein $R^4$ and $Z_1$ are the same as defined above) in a similar manner described in Step A-1, B-1, C-1, D-1 and E-1.

In Step F-2, compounds of the formula (XIV) (wherein $R^1$, $R^4$ and $Z_1$ are the same as defined above) can be prepared by the reduction of compounds of the formula (XIII) (wherein $R^1$, $R^4$ and $Z_1$ are the same as defined above) by hydrogenation using a catalyst including, for instance, palladium on carbon and platinum on carbon in the presence of a base such as potassium acetate.

The reaction can be carried out in a solvent including, for instance, ethers such as diethyl ether, isopropyl ether, dioxane, tetrahydrofuran (THF) and 1,2-dimethoxyethane, aromatic hydrocarbons such as benzene, toluene and xylene, alcohols such as methanol, ethanol, 1-propanol, isopropanol and tert-butanol, water and others.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

In Step F-3, compounds of the formula (I-f) (wherein $R^1$ and $R^4$ are the same as defined above) can be prepared by the removal of protective group $Z_1$ of compounds of the formula (XIV) (wherein $R^1$, $R^4$ and $Z_1$ are the same as defined above) in a similar manner of Step A-2 for the preparation of compounds of the formula (I-a).

[Method G]

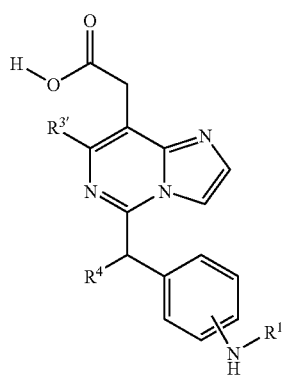

Compounds of the formula (I-g) (wherein $R^1$ and $R^4$ are the same as defined above and $R^3$ has the same significance as $R^3$ as defined above excluding hydrogen and halogen), can be prepared by the following procedures.

In Step G-1, compounds of the formula (XVI) (wherein $R^1$, $R^{3'}$, $R^4$ and $Z_1$ are the same as defined above) can be prepared by the reaction of compounds of the formula (XIII) (wherein $R^1$, $R^4$ and $Z_1$ are the same as defined above) with compounds of the formula (XV) (wherein $R^3$ is the same as defined above).

The reaction may be carried out without solvent or in a solvent including, for instance, ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methyl-pyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

The reaction can be advantageously carried out in the presence of a base including, for instance, organic amines such as pyridine, triethylamine, N,N-diisopropylethylamine, dimethylaniline, diethylaniline, and others.

In Step G-2, compounds of the formula (I-g) (wherein $R^1$, $R^3$ and $R^4$ are the same as defined above) can be prepared by the removal of protective group $Z_1$ of compounds of the formula (XVI) (wherein $R^1$, $R^{3'}$, $R^4$ and $Z_1$ are the same as defined above) in a similar manner of Step A-2 for the preparation of compounds of the formula (I-a).

[Method H]

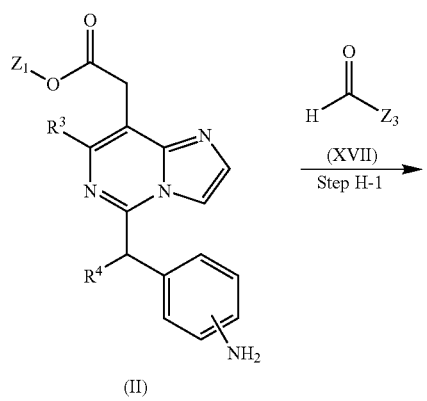

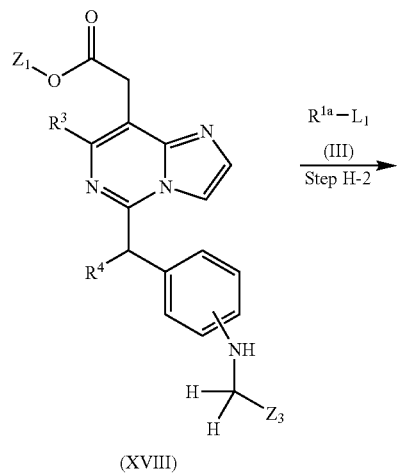

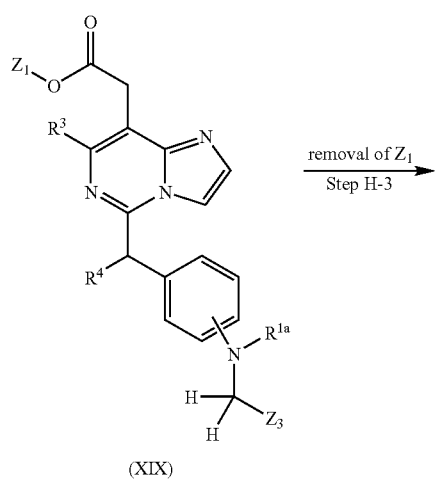

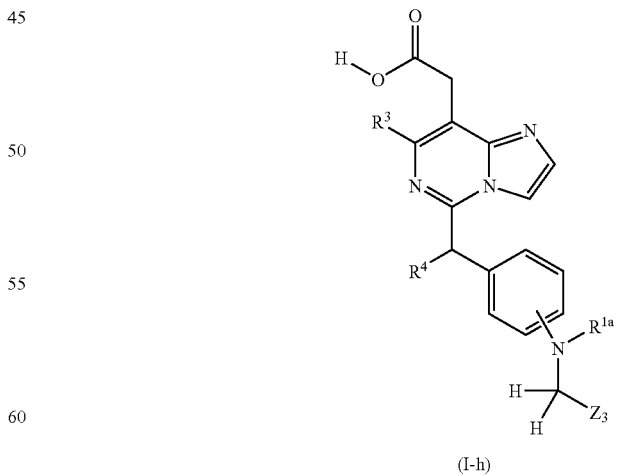

Compounds of the formula (I-h) (wherein $R^3$ and $R^4$ are the same as defined above, $R^{1a}$ represents

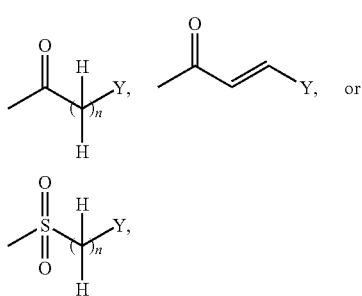

in which n and Y are the same as defined above and $Z_3$ represents hydrogen or $C_{1-5}$ alkyl) can also be prepared by the following procedures.

In Step H-1, compounds of the formula (XVIII) (wherein $R^3$, $R^4$, $Z_1$ and $Z_3$ are the same as defined above) can be prepared by the reaction of compounds of the formula (II) (wherein $R^3$, $R^4$ and $Z_1$ are the same as defined above) with compounds of the formula (XVII) (wherein $Z_3$ is the same as defined above) in a similar manner described in Step B-1 for the preparation of compounds of the formula (VI).

In Step H-2, compounds of the formula (XIX) (wherein $R^{1a}$, $R^3$, $R^4$, $Z_1$ and $Z_3$ are the same as defined above and represents) can be prepared by the reaction of compounds of the formula (XVII) (wherein $R^3$, $R^4$, $Z_1$ and $Z_3$ are the same as defined above) with compounds of the formula (III) (wherein $R^{1a}$ and $L_1$ are the same as defined above) in a similar manner described in Step A-1 for the preparation of compounds of the formula (IV).

In Step H-3, compounds of the formula (I-h) (wherein $R^{1a}$, $R^3$, $R^4$ and $Z_3$ are the same as defined above) can be prepared by the removal of protective group $Z_1$ of compounds of the formula (XIX) (wherein $R^{1a}$, $R^3$, $R^4$, $Z_1$ and $Z_3$ are the same as defined above) in a similar manner of Step A-2 for the preparation of compounds of the formula (I-a).

Compounds of the formula (XVII) are commercially available or can be synthesized by conventional methods.

[Method I]

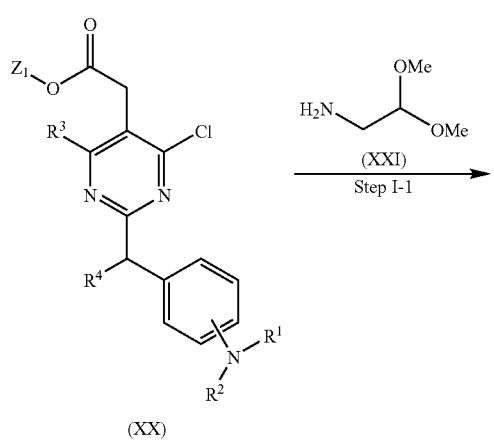

(XX)

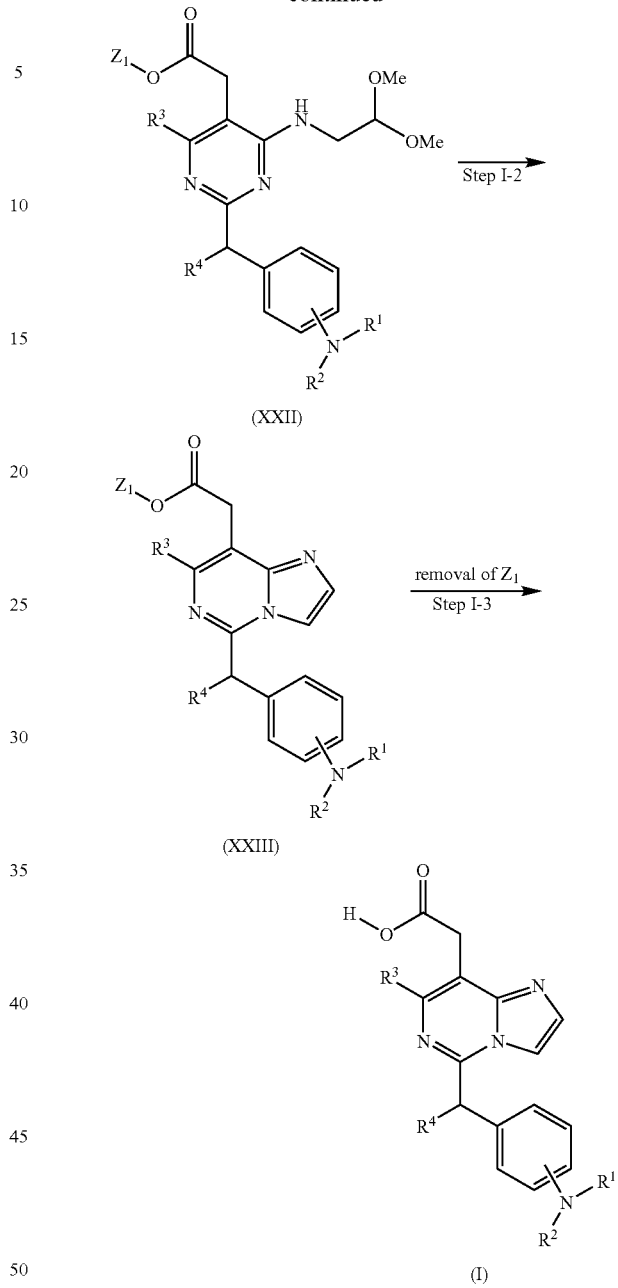

Compounds of the formula (I) (wherein $R^1$, $R^2$, $R^3$ and $R^4$ are the same as defined above) can be prepared by the following procedures.

In Step I-1, compounds of the formula (XXII) (wherein $R^1$, $R^2$, $R^3$, $R^4$ and $Z_1$ are the same as defined above) can be prepared by the reaction of compounds of the formula (XX) (wherein $R^1$, $R^2$, $R^3$, $R^4$ and $Z_1$ are the same as defined above) with compounds of the formula (XXI).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydro-carbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction can be advantageously carried out in the presence of a base including, for instance, organic amines such as triethylamine and N,N-diisopropylethylamine, and others.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

In Step I-3, compounds of the formula (I) (wherein $R^1$, $R^2$, $R^3$ and $R^4$ are the same as defined above) can be prepared by the removal of protective group $Z_1$ of compounds of the formula (XXIII) (wherein $R^1$, $R^2$, $R^3$, $R^4$ and $Z_1$ are the same as defined above) in a similar manner of Step A-2 for the preparation of compounds of the formula (I-a).

Compounds of the formula (XX) and (XXI) are commercially available or can be, synthesized by conventional methods.

Preparation of Starting Compounds

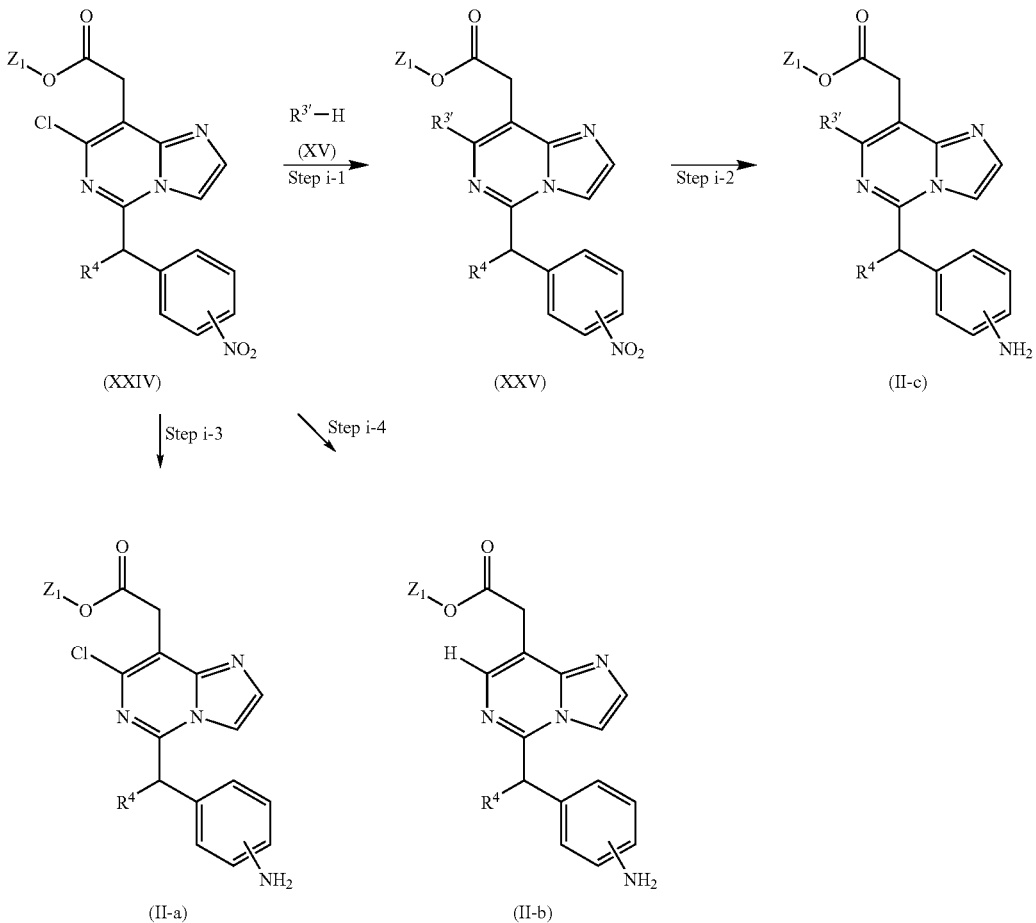

about 20° C. to 100° C. The reaction may be conducted for, usually, 30 minutes to 24 hours and preferably 1 to 12 hours.

In Step I-2, compounds of the formula (XXIII) (wherein $R^1$, $R^2$, $R^3$, $R^4$ and $Z_1$ are the same as defined above) can be prepared by the reaction of compounds of the formula (XXII) (wherein $R^1$, $R^2$, $R^3$, $R^4$ and $Z_1$ are the same as defined above).

The reaction can be carried out in the presence of an agent including, for instance, acid such as hydrochloric acid and trifluoroacetic acid, trifluoroacetic anhydride, or POCl$_3$, and the like.

The reaction temperature can be optionally set depending on the compounds to be reacted. The reaction temperature is usually, but not limited to, about 0° C. to 180° C., preferably Compounds of the formula (II-c) (wherein $R^{3'}$, $R^4$ and $Z_1$ are the same as defined above) can be, for instance, prepared by the following procedures in two steps.

In Step i-1, compounds of the formula (XXIV) (wherein $R^4$ and $Z_1$ are the same as defined above) is reacted with compounds of the formula (XV) (wherein $R^{3'}$ is the same as defined above) to give compounds of the formula (XXV) (wherein $R^{3'}$, $R^4$ and $Z_1$ are the same as defined above).

The reaction may be carried out without solvent or in a solvent including, for instance, ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methyl-pyrrolidone (NUT); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

The reaction can be advantageously carried out in the presence of a base including, for instance, organic amines such as pyridine, triethylamine, N,N-diisopropylethylamine, dimethylaniline, diethylaniline, and others.

In Step i-2, compounds of the formula (II-c) (wherein $R^{3'}$, $R^4$ and $Z_1$ are the same as defined above) can be prepared by reducing the nitro group of compounds of the formula (XXV) (wherein $R^{3'}$, $R^4$ and $Z_1$ are the same as defined above) using an agent including, for instance, metals such as zinc and iron in the presence of acid including, for instance, hydrochloric acid and acetic acid and stannous chloride, or by hydrogenation using a catalyst including, for instance, palladium on carbon and platinum on carbon.

The reaction can be carried out in a solvent including, for instance, ethers such as diethyl ether, isopropyl ether, dioxane, tetrahydrofuran (THF) and 1,2-dimethoxyethane, aromatic hydrocarbons such as benzene, toluene and xylene, alcohols such as methanol, ethanol, 1-propanol, isopropanol and tert-butanol, water and others.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

Compounds of the formula (II-a) (wherein $R^4$ and $Z_1$ are the same as defined above) can be prepared by reducing the nitro group of compounds of the formula (XXIV) (wherein $R^4$ and $Z_1$ are the same as defined above) in a similar manner described in Step i-2 for the preparation of compounds of the formula (II-c), as shown in Step i-3.

Compounds of the formula (II-b) (wherein $R^4$ and $Z_1$ are the same as defined above) can be prepared by reducing the chloro group and nitro group of compounds of the formula (XXIV) (wherein $R^4$ and $Z_1$ are the same as defined above) by hydrogenation using a catalyst including, for instance, palladium on carbon and platinum on carbon in the presence of a base such as potassium acetate, as shown in Step i-4.

The reaction can be carried out in a solvent including, for instance, ethers such as diethyl ether, isopropyl ether, dioxane, tetrahydrofuran (THF) and 1,2-dimethoxyethane, aromatic hydrocarbons such as benzene, toluene and xylene, alcohols such as methanol, ethanol, 1-propanol, isopropanol and tert-butanol, water and others.

The reaction temperature can be optionally set depending on the compounds to be reacted. The reaction temperature is usually, but not limited to, about 0° C. to 180° C., preferably about 20° C. to 100° C. The reaction may be conducted for, usually, 30 minutes to 24 hours and preferably 1 to 12 hours.

Preparation of Compounds of the Formula (XXIV)

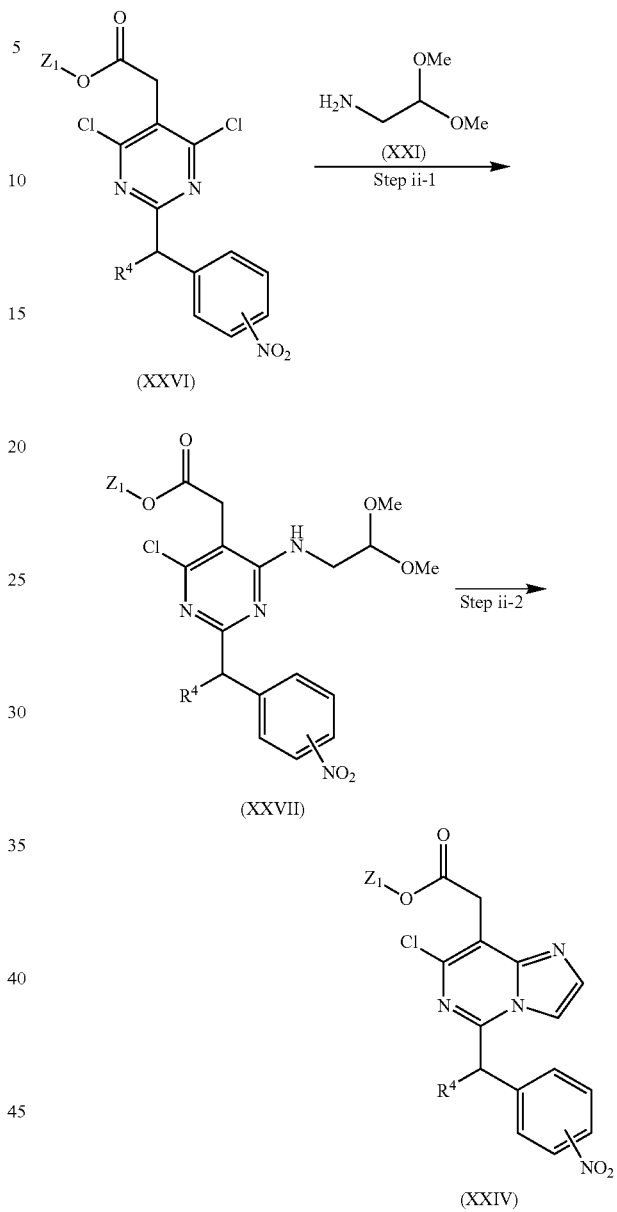

Compounds of the formula (XXIV) (wherein $R^4$ and $Z_1$ are the same as defined above) can be, for instance, prepared by the following procedures.

In Step ii-1, compounds of the formula (XXVII) (wherein $R^4$ and $Z_1$ are the same as defined above) can be prepared by the reaction of compounds of the formula (XXVI) (wherein $R^4$ and $Z_1$ are the same as defined above) with compounds of the formula (XXI) in a similar manner described in Step I-1 for the preparation of compounds of the formula (XXII).

In Step ii-2, compounds of the formula (XXIV) (wherein $R^4$ and $Z_1$ are the same as defined above) can be prepared by the reaction of compounds of the formula (XXVII) (wherein $R^4$ and $Z_1$ are the same as defined above) in a similar manner described in Step I-2 for the preparation of compounds of the formula (XXIII).

Preparation of Compounds of the Formula (XXVI)

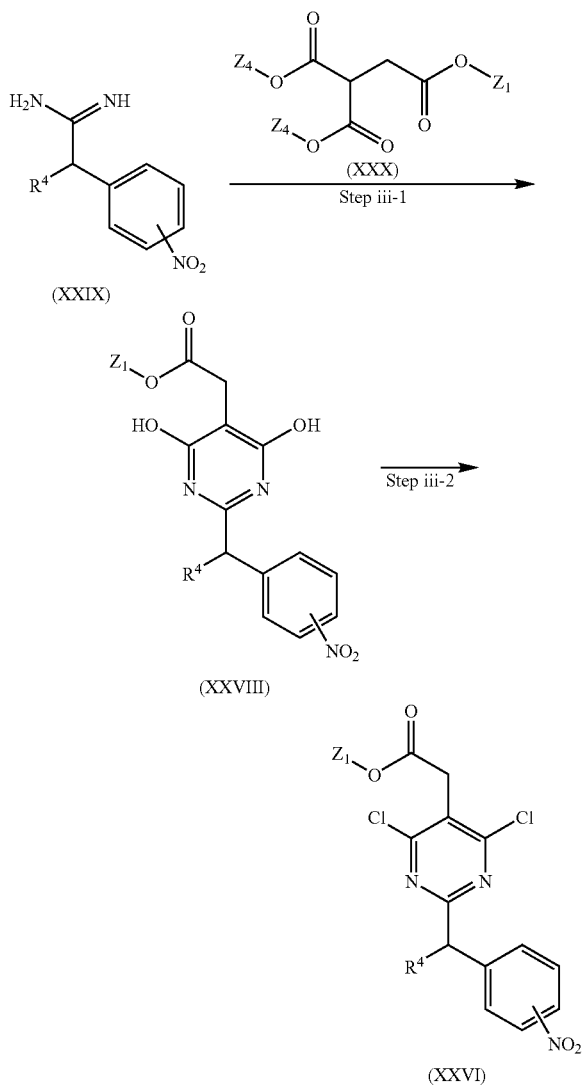

Compounds of the formula (XXVI) (wherein $R^4$ and $Z_1$ are the same as defined above) can be, for instance, prepared by the following procedures.

In Step iii-1, compounds of the formula (XXVIII) (wherein $R^4$ and $Z_1$ are the same as defined above) can be prepared by the reaction of compounds of the formula (XXIX) (wherein $R^4$ is the same as defined above) with compounds of the formula (XXX) (wherein $Z_1$ is the same as defined above and $Z_4$ is $C_{1-6}$ alkyl)

The reaction can be advantageously carried out in the presence of a base such as sodium methoxide.

The reaction may be carried out in a solvent including, for instance, alcohols such as methanol, ethanol, 1-propanol, isopropanol and tert-butanol.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step iii-2, compounds of the formula (XXVI) (wherein $R^4$ and $Z_1$ are the same as defined above) can be prepared for instance, by the reaction of compounds of the formula (XXVIII) (wherein $R^4$ and $Z_1$ are the same as defined above) with an appropriate halogenating reagent including, for instance, $POCl_3$, $PCl_5$, and the like.

The reaction may be carried out without solvent or in a solvent including, for instance, halogenated hydrocarbons such as dichloromethane, chloroform and 1,2-dichloroethane, aromatic hydrocarbons such as benzene, toluene, and xylene, and others. Optionally, two or more of the solvents selected from the listed above can be mixed and used.

The reaction can be advantageously conducted in the presence of a base, including, for instance, pyridine, triethylamine and N,N-diisopropylethylamine, N,N-dimethylaniline, diethylaniline, and others.

The reaction temperature is usually, but not limited to, about 40° C. to 200° C. and preferably about 20° C. to 180° C. The reaction may be conducted for, usually, 30 minutes to 48 hours and preferably 2 hour to 12 hours.

Compounds of the formula (XXIX) is commercially available or can be synthesized by conventional methods.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydriodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethyl-amine, tris (hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

The compound of the present invention or salts thereof, depending on its substituents, may be modified to form lower alkylesters or known other esters; and/or hydrates or other solvates. Those esters, hydrates, and solvates are included in the scope of the present invention.

The compound of the present invention may be administered in oral forms, such as, without limitation, normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically-acceptable excipients. Excipients are inert substances such as, without limitation, carriers, diluents, flavoring agents, sweeteners, lubricants, solubilizers, suspending agents, binders, tablet disintegrating agents and encapsulating material.

Yet another embodiment of the present invention is pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically-acceptable excipients therefore. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills, powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the compound of the present invention, when used for the indicated effects, will range from about 1 mg/kg/day to about 10 mg/kg/day. The compounds of the present invention may be administered in a single daily dose, or the total daily dose may be administered in divided doses, two, three, or more times per day. Where delivery is via transdermal forms, of course, administration is continuous.

EXAMPLES

The present invention will be described as a form of examples, but they should by no means be construed as defining the metes and bounds of the present invention.

In the examples below, all quantitative data, if not stated otherwise, relate to percentages by weight.

Mass spectra were obtained using electrospray (ES) ionization techniques (micromass Platform LC). Melting points are uncorrected. Liquid Chromatography-Mass spectroscopy (LC-MS) data were recorded on a Micromass Platform LC with Shimadzu Phenomenex ODS column (4.6 mm$\phi$×30 mm) flushing a mixture of acetonitrile-water (9:1 to 1:9) at 1 ml/min of the flow rate. TLC was performed on a precoated silica gel plate (Merck silica gel 60 F-254). Silica gel (WAKO-gel C-200 (75-150 μm)) was used for all column chromatography separations. All chemicals were reagent grade and were purchased from Sigma-Aldrich, Wako pure chemical industries, Ltd., Great Britain, Tokyo kasei kogyo Co., Ltd., Nacalai tesque, Inc., Watanabe Chemical Ind. Ltd., Maybridge plc, Lancaster Synthesis Ltd., Merck KgaA, Germany, Kanto Chemical Co., Ltd.

$^1$H NMR spectra were recorded using either Bruker DRX-300 (300 MHz for $^1$H) spectrometer or Brucker 500 UltraShieled™ (500 MHz for $^1$H). Chemical shifts are reported in parts per million (ppm) with tetramethylsilane (TMS) as an internal standard at zero ppm. Coupling constant (J) are given in hertz and the abbreviations s, d, t, q, m, and br refer to singlet, doublet, triplet, quartet, multiplet, and broad, respectively. The mass determinations were carried out by MAT95 (Finnigan MAT).

All starting materials are commercially available or can be prepared using methods cited in the literature.

The effect of the present compounds was examined by the following assays and pharmacological tests.

Example 1

Preparation of Human CRTH2-Transfected L1.2 Cell Line

Human CRTH2 cDNA was amplified from human eosinophil cDNA with gene specific primers containing restriction sites for cloning into pEAK vector (Edge Bio Systems). The human CRTH2 cDNA was cloned into the mammalian expression vector pEAK. This expression plasmid (40 μg) was transfected into L1.2 cells, at a cell density of 1×10$^7$ cells/500 μl, by using electroporation apparatus (Gene Pulser II, BioRad) at 250V/1,000 μF. One day after the transfection, puromycin (1 μg/ml, Sigma) was added into the cell culture plates. Two weeks after the transfection, grown cells were picked up for further growth.

[Measurement of $Ca^{2+}$ Mobilization in the Human CRTH2-Transfected L1.2 Cell Line] (Assay 1)

$Ca^{2+}$ loading buffer was prepared by mixing 5 μl of Fluo-3AM (2 mM in DMSO, final 1 μM, Molecular Probes) and 10 μl of pluronic F-127 (Molecular Probes) and diluting the resulting mixture in 10 ml of $Ca^{2+}$ assay buffer (20 mM HEPES pH 7.6, 0.1% BSA, 1 mM probenecid, Hanks' solution). The CRTH2 transfected cells which were prepared in Example 1 were washed with PBS, resuspended in $Ca^{2+}$ loading buffer at $1\times10^7$ cells/ml, and incubated for 60 min at room temperature. After incubation, cells were washed and resuspended in $Ca^{2+}$ assay buffer, then dispensed into transparent-bottom 96-well plates (#3631, Costar) at $2\times10^5$ cells/well. Cells were incubated with various concentrations of test compound for 5 minutes at room temperature. The emitted 480 nm fluorescence was measured on FDSS6000, a $Ca^{2+}$-measurement apparatus (Hamamatsu Photonics, Hamamatsu, Japan). The transfectant showed $PGD_2$-induced $Ca^{2+}$ mobilization in a concentration-dependent manner.

[Human CRTH2 Receptor Binding Assay] (Assay 2)

CRTH2 transfectants were washed once with PBS and resuspended in binding buffer (50 mM Tris-HCl, pH7.4, 40 mM $MgCl_2$, 0.1% BSA, 0.1% $NaN_3$). 100 μl of cell suspension ($2\times10^5$ cells), [$^3$H]-labeled $PGD_2$, and various concentrations of test compound were then mixed in a 96-well U-bottom polypropylene plate and incubated for 60 min at room temperature to allow binding to occur. After incubation, the cell suspension was transferred to a filtration plate (#MAFB, Millipore) and washed 3 times with binding buffer. Scintillant was added to the filtration plate, and radioactivity remaining on the filter was measured by TopCount (Packard), a scintillation counter. Non-specific binding was determined by incubating the cell suspension and [$^3$H]-labeled $PGD_2$ in the presence of 1 μM of unlabeled $PGD_2$. Puromycin-resistant L1.2 transfectants bound to [$^3$H]-labeled $PGD_2$ with high affinity ($K_D$=6.3 nM).

[Migration Assay of Human Eosinophils] (Assay 3)

Human polymorphonuclear cells were isolated from heparinized venous blood of healthy donors by laying the blood on Mono-Poly Resolving Medium (ICN Biomedicals, Co. Ltd) and centrifuging it at 400×g for 30 min. at room temperature. After centrifugation, eosinophils were purified from the lower layer of polymorphonuclear cells by CD16-negative selection using anti-CD16-conjugated magnetic beads (Miltenyi Biotech GmbH).

Human eosinophils were washed with PBS and resuspended in chemotaxis buffer (20 mM HEPES pH 7.6, 0.1% BSA, Hanks' solution) at $6\times10^6$ cells/ml. Fifty μl of the cell suspension ($3\times10^5$ cells/well) was then dispensed into the upper chamber and 30 μl of ligand solution ($PGD_2$, 1 mM, final concentration) was added to the lower chamber of a 96-well chemotaxis chamber (Diameter=5 μm, #106-5, Neuro Probe). Cells were preincubated with various concentrations of test compound at 37° C. for 10 minutes. Chemotaxis is then allowed to occur in a humidified incubator at 37° C., 5% $CO_2$ for 2 hours. The number of cells migrating into the lower chamber was counted by FACScan (Becton-Dickinson).

[Migration Assay of Human CD4+ T Cells] (Assay 4)

Human mononuclear cells were isolated from heparinized venous blood of healthy donors by laying the blood on Mono-Poly Resolving Medium (ICN Biomedicals, Co. Ltd) and centrifuging it at 400×g for 30 min. at room temperature. After centrifugation, CD4$^+$ T lymphocytes were purified from mononuclear cells by using CD4$^+$ T cell isolation kit (Miltenyi Biotec GmbH).

Human CD4$^+$ T lymphocytes were washed with PBS and resuspended in chemotaxis buffer (20 mM HEPES pH 7.6, 0.1% BSA, Hanks' solution) at $6\times10^6$ cells/ml. Fifty μl of the cell suspension ($3\times10^5$ cells/well) was then dispensed into the upper chamber and 30 μl of ligand solution ($PGD_2$, 10 nM, final concentration) was added to the lower chamber of a 96-well chemotaxis chamber (Diameter=3 mm, #106-3, Neuro Probe). Cells were preincubated with various concentrations of test compound at 37° C. for 10 minutes. Chemotaxis is then allowed to occur in a humidified incubator at 37° C., 5% $CO_2$ for 4 hours. The number of cells migrating into the lower chamber was counted by FACScan (Becton-Dickinson).

Assay results in Assay 1 are shown in Examples and tables of the Examples below. The data corresponds to the compounds as yielded by solid phase synthesis and thus to levels of purity of about 40 to 90%. For practical reasons, the compounds are grouped in four classes of activity as follows:

$IC_{50}=A(<$ or $=)10$ nM$<B(<$ or $=)100$ nM$<C$ $(<$ or $=)500$ nM$<D$

The compounds of the present invention also show excellent selectivity, and potent activity in Assays 2, 3 and 4 described above.

Z used in Melting point in the following section indicates decomposition. All inorganic acids and bases were aqueous solutions unless otherwise stated. Eluent concentrations are expressed as % vol./vol.

Preparation of Compounds

Methyl [4,6-dichloro-2-(4-nitrobenzyl)pyrimidin-5-yl]acetate

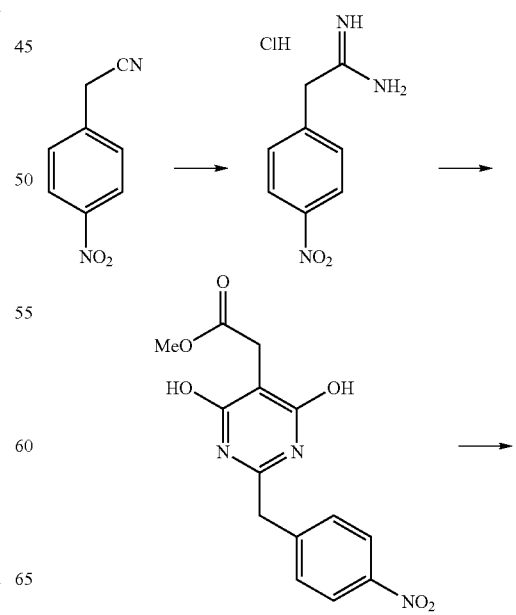

Methyl [7-chloro-5-(4-nitrobenzyl)imidazo[1,2-c]pyrimidin-8-yl]acetate

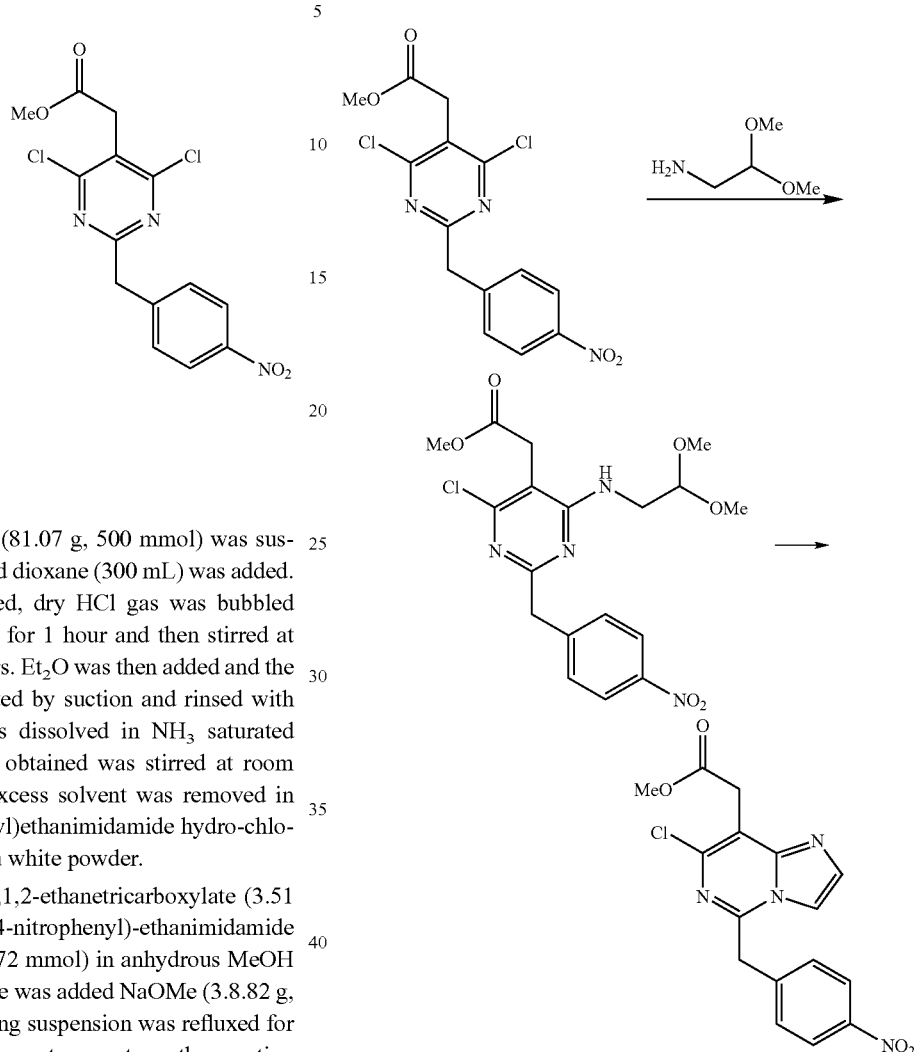

4-Nitrophenyl acetonitrile (81.07 g, 500 mmol) was suspended in EtOH (300 mL) and dioxane (300 mL) was added. After all solids had dissolved, dry HCl gas was bubbled through the reaction mixture for 1 hour and then stirred at room temperature for 15 hours. $Et_2O$ was then added and the separated solids were collected by suction and rinsed with $Et_2O$. This intermediate was dissolved in $NH_3$ saturated EtOH and the solution thus obtained was stirred at room temperature for 14 hours. Excess solvent was removed in vacuo to give 2-(4-nitrophenyl)ethanimidamide hydro-chloride (73.65 g, 68% yield) as a white powder.

To a mixture of triethyl 1,1,2-ethanetricarboxylate (3.51 mL, 15.30 mmol) and 2-(4-nitrophenyl)-ethanimidamide hydrochloride (46.95 g, 217.72 mmol) in anhydrous MeOH (300 mL) at room temperature was added NaOMe (3.8.82 g, 718.49 mmol) and the resulting suspension was refluxed for 16 hours. After cooling to room temperature, the reaction mixture was chilled to 0° C., acidified with 6N HCl, and the separated solids collected by suction and rinsed with cold water. Drying under high vacuum at 45° C. for 6 hours then gave methyl [4,6-dihydroxy-2-(4-nitrobenzyl)-pyrimidin-5-yl]acetate (56.48 g, 81% yield) as a pale white powder.

To a suspension of methyl [4,6-dihydroxy-2-(4-nitrobenzyl)pyrimidin-5-yl]acetate (4.12 g, 12.89 mmol) in $POCl_3$ (24 mL) at room temperature and under Ar atmosphere was added N,N-dimethylaniline (8.17 mL, 64.44 mmol) and the resulting dark suspension was heated at reflux for 16 hours. After cooling to room temperature, excess $POCl_3$ was evaporated and the remaining dark residue was dissolved in EtOAc. This organic layer was then washed sequentially with saturated $NaHCO_3$, water, and brine, dried over anhydrous $MgSO_4$, filtered, and concentrated in vacuo. The crude product thus obtained was dissolved in $CH_2Cl_2$ and passed through a short plug of silica gel to afford pure methyl [4,6-dichloro-2-(4-nitrobenzyl)pyrimidin-5-yl]acetate (2.98 g, 65% yield) as an off-white powder.

A mixture of methyl [4,6-dichloro-2-(4-nitrobenzyl)pyrimidin-5-yl]acetate (2.0 g, 5.6 mmol), aminoacetaldehyde dimethylacetal (0.68 g, 6.5 mmol) and diisopropylethylamine (1.5 mL, 8.4 mmol) in 1,4-dioxane (50 mL) was stirred at 80° C. for 2 hours. The mixture was concentrated under reduced pressure. The residue was extracted with ethyl acetate. The extracts were washed with aq $NaHCO_3$ and brine, dried over sodium sulfate, filtered and concentrated under reduced pressure. The crude product was purified by preparative MPLC (silica gel, hexane:ethyl acetate, 2/1) to give methyl [4-chloro-6-[(2,2-dimethoxyethyl)amino]-2-(4-nitrobenzyl)pyrimidin-5-yl]-acetate (1.89 g, 79%) as a gray solid.

Methyl [4-chloro-6-[(2,2-dimethoxyethyl)amino]-2-(4-nitrobenzyl)pyrimidin-5-yl]acetate (100 mg, 0.19 mmol) was treated with 50% trifluoroacetic acid/dichloromethane (5 mL) at room temperature overnight. The mixture was poured into water and extracted with dichloromethane. The extracts were washed with aq $NaHCO_3$ and brine, dried over magnesium sulfate, filtered and concentrated under reduced pressure. The crude product was dissolved in dichloromethane (5 mL). To the solution was added trifluoroacetic anhydride (0.053 mL, 0.38 mmol). The mixture was stirred at room temperature for 3 hours. The mixture was poured into water and extracted with dichloromethane. The extracts were washed with aq NaHCO₃ and brine, dried over magnesium sulfate, filtered and concentrated under reduced pressure. The crude product was purified by preparative TLC (silica gel, chloroform:ethanol, 19/1) to give methyl [7-chloro-5-(4-nitrobenzyl)imidazo[1,2-c]pyrimidin-8-yl]acetate (22 mg, 25%) as a colorless film.

Methyl [7-chloro-5-(4-aminobenzyl)imidazo[1,2-c]pyrimidin-8-yl]acetate

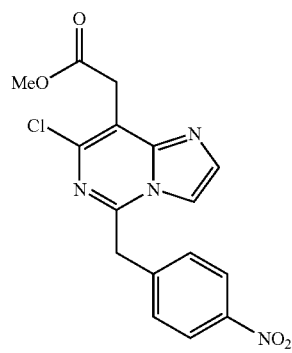

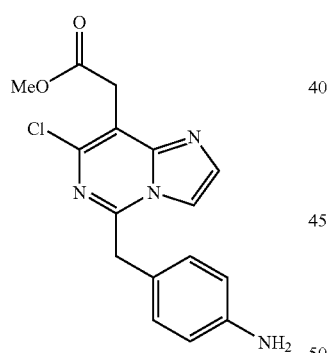

A mixture of methyl [7-chloro-5-(4-nitrobenzyl)imidazo[1,2-c]pyrimidin-8-yl]acetate (0.383 g, 1.06 mmol) and SnCl₂.2H₂O (1.44 g, 6.37 mmol) in EtOH (5 mL) was heated at refluxing temperature for 1 hour. After cooling to room temperature, the reaction mixture was poured into sat. NaHCO₃ aq. and EtOAc and the resulting white suspension was filtered through a pad of Celite. The aqueous layer was separated and extracted with EtOAc. The combined organic extracts was washed with brine, dried over anhydrous MgSO₄, filtered, and concentrated in vacuo to give methyl [7-chloro-5-(4-aminobenzyl)imidazo[1,2-c]pyrimidin-8-yl]acetate (0.322 g, 92%).

Example 1-1

[7-Chloro-5-(4-{[4-(trifluoromethyl)benzoyl]amino}benzyl)imidazo[1,2-c]pyrimidin-8-yl]acetic acid

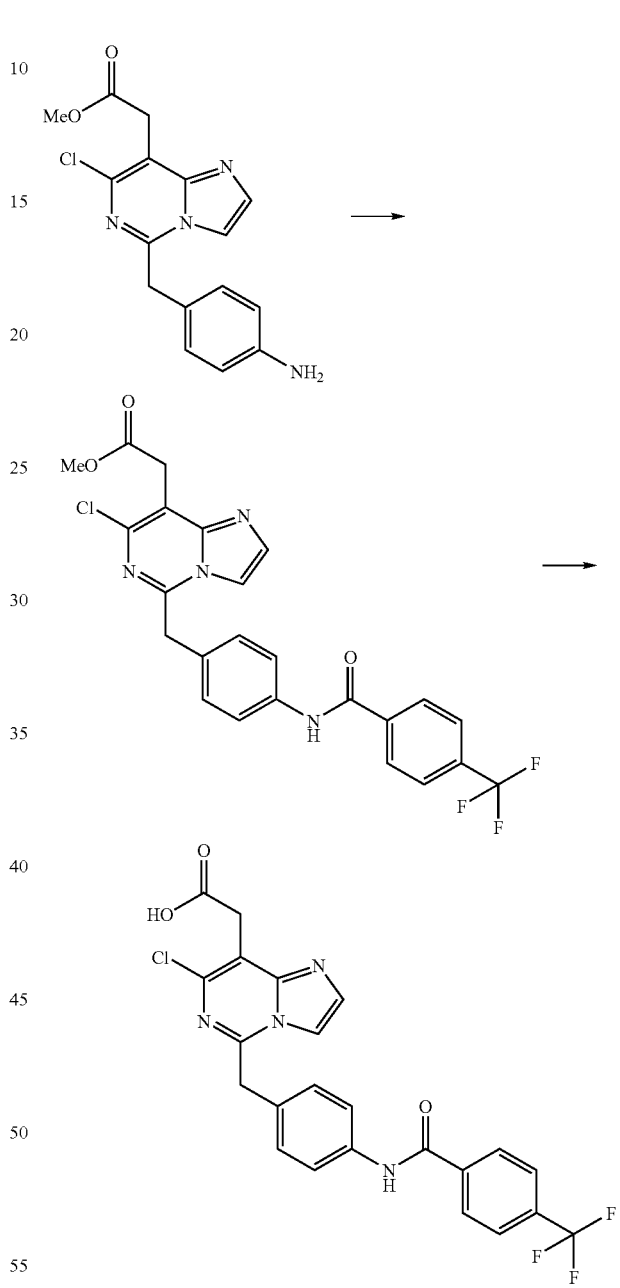

To a solution of methyl [7-chloro-5-(4-aminobenzyl)imidazo[1,2-c]pyrimidin-8-yl]acetate (0.081 g, 0.243 mmol), 3,4-dichlorobenzoic acid (0.070 g, 0.365 mmol), and WSCI (0.070 g, 0.365 mmol) in CH₂Cl₂ (5 mL) was added N,N-diisopropylethyl amine (0.127 mL, 0.730 mmol). After stirring at room temperature for 20 hours, the reaction mixture was condensed under reduced pressure to give the crude product as a thick oil which was purified by silica gel chromatography eluting with 30% EtOAc in CHCl₃ to give methyl

[7-Chloro-5-(4-{[4-(trifluoromethyl)benzoyl]-amino}benzyl)imidazo[1,2-c]pyrimidin-8-yl]acetate as a white solid (0.100 gi 82%).

A solution of methyl [7-Chloro-5-(4-{[4-(trifluoromethyl)benzoyl]amino}benzyl)imidazo[1,2-c]-pyrimidin-8-yl]acetate (0.100 g, 0.199 mmol) in dioxane (1.00 mL) was added 6N HCl aq. (0.5 mL) and heated to 100° C. for 22 hours. After cooling to room temperature, the volatiles was removed under reduced pressure to generate a precipitate which was suspended in water, collected by suction, rinsed with water and diethyl ether, and dried under high vacuum to give [7-chloro-5-(4-{[4-(trifluoromethyl)benzoyl]amino}benzyl)imidazo[1,2-c]pyrimidin-8-yl]acetic acid as a white powder (0.020 g, 20%).

$^1$H-NMR (500 MHz, DMSO-d$_6$): δ 3.96 (s, 2H), 4.52 (s, 2H), 7.39 (d, J=8 Hz, 2H), 7.73 (d, J=1.5 Hz, 1H), 7.74 (d; J=8 Hz, 2H), 7.91 (d, J=8 Hz, 2H), 8.13 (d, J=8 Hz, 2H), 8.19 (d, J=1.5 Hz, 1H), 10.48 (s, 1H), 12.71 (br s, 1H)

Melting point: 201Z° C.

Molecular weight: 488.85

Mass spectrometry: 489

In vitro activity grade: B

In a similar manner as described in Example 1-1, compounds in Example 1-2 to 1-5 as shown in Table 1 were synthesized.

TABLE 1

| example # | Structure | MW | Exact Mass | MS | mp (° C.) | Activity class |
|---|---|---|---|---|---|---|
| 1-2 | 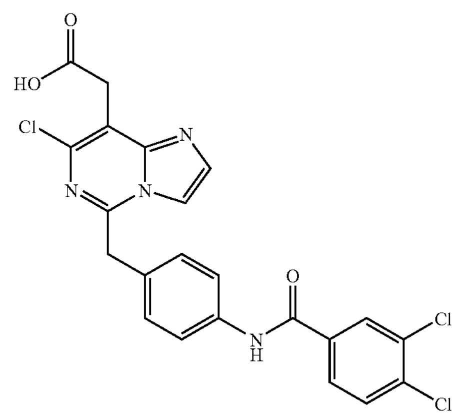 | 489.75 | 488 | 489 | 180Z | A |
| 1-3 | 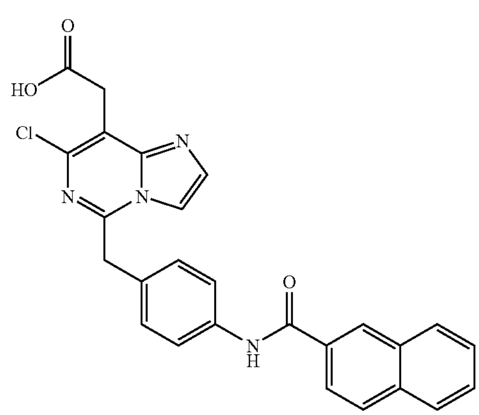 | 470.92 | 470 | 471 | 204Z | B |

TABLE 1-continued

| example # | Structure | MW | Exact Mass | MS | mp (° C.) | Activity class |
|---|---|---|---|---|---|---|
| 1-4 | 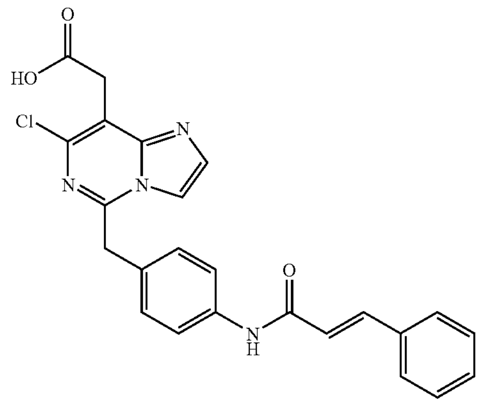 | 446.90 | 446 | 447 | 184Z | A |
| 1-5 | 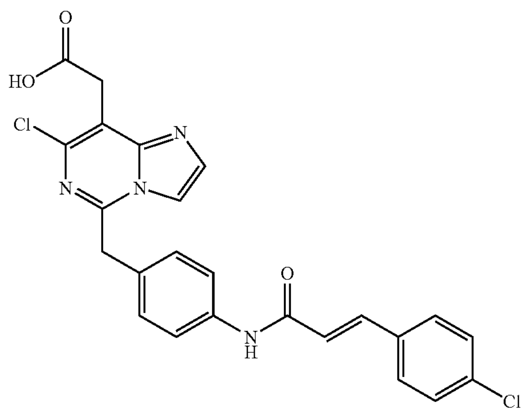 | 481.34 | 480 | 481 | 205Z | B |

Methyl [5-(4-aminobenzyl)imidazo[1,2-c]pyrimidin-8-yl]acetate

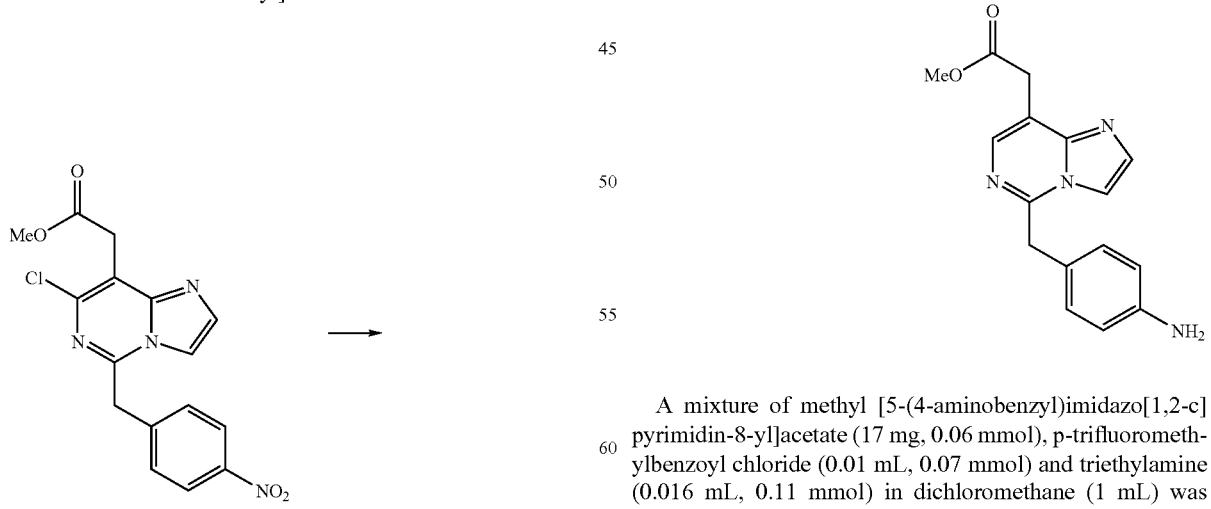

A mixture of methyl [5-(4-aminobenzyl)imidazo[1,2-c]pyrimidin-8-yl]acetate (17 mg, 0.06 mmol), p-trifluoromethylbenzoyl chloride (0.01 mL, 0.07 mmol) and triethylamine (0.016 mL, 0.11 mmol) in dichloromethane (1 mL) was stirred at room temperature for 1 hour. The reaction was quenched with water, and extracted with chloroform. The extracts were washed with water and brine, dried over sodium sulfate, filtered and concentrated under reduced pressure. The crude product was purified by preparative TLC (silica gel, chloroform:methanol, 95/5) to give methyl [5-(4-{[4-(trifluoromethyl)benzoyl]amino}benzyl)imidazo[1,2-c]pyrimidin-8-yl]acetate (21.5 mg, 80%) as slightly yellow solid.

Example 2-1

[5-(4-{[4-(trifluoromethyl)benzoyl]amino}benzyl)imidazo[1,2-c]pyrimidin-8-yl]acetic acid

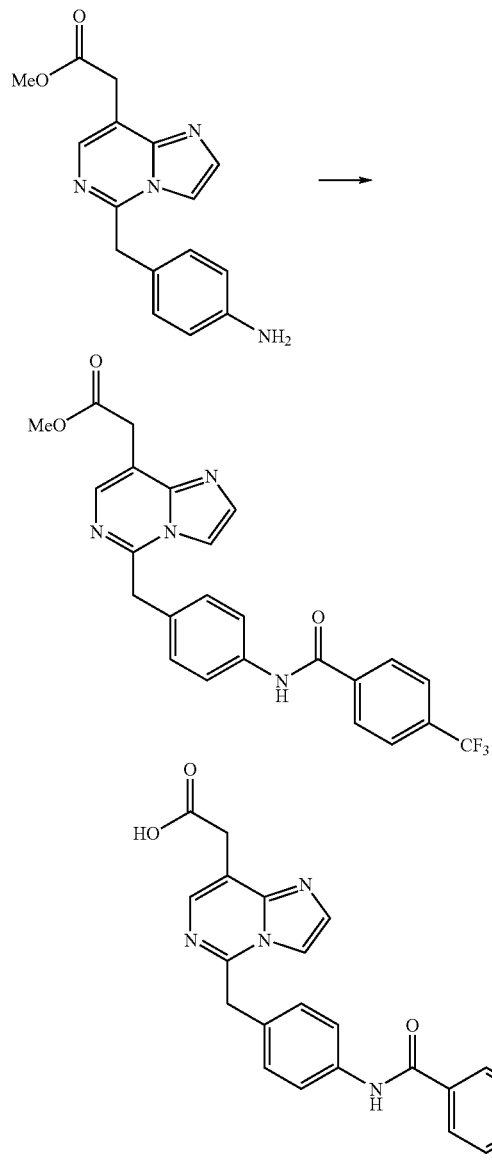

A mixture of methyl [5-(4-aminobenzyl)imidazo[1,2-c]pyrimidin-8-yl]acetate (17 mg, 0.06 mmol), p-trifluoromethylbenzoyl chloride (0.01 mL, 0.07 mmol) and triethylamine (0.016 mL, 0.11 mmol) in dichloromethan (1 mL) was stirred at room temperature for 1 hour. The reaction was quenched with water, and extracted with chloroform. The extracts were washed with water and brine, dried over sodium sulfate, filtered and concentrated under reduced pressure. The crude product was purified by preparative TLC (silica gel, chloroform:methanol, 95/5) to give methyl [5-(4-{[4-(trifluoromethyl)benzoyl]amino}benzyl)imidazo[1,2-c]pyrimidin-8-yl]acetate (21.5 mg, 80%) as slightly yellow solid.

To a solution of methyl [5-(4-{[4-(trifluoromethyl)benzoyl]amino}benzyl)imidazo[1,2-c]-pyrimidin-8-yl]acetate (20 mg, 0.04 mmol) in methanol (1 mL) was added 1M NaOH aqueous solution (0.2 mL) at room temperature, and the mixture was stirred for 1 hour. After the removal of methanol under reduced pressure, water was added to the residue. The solution was washed with diethyl ether and neutralized by aqueous hydrochloric acid. The resulting precipitates were collected by filtration and dried under reduced pressure to give [5-(4-{[4-(trifluoromethyl)-benzoyl]amino}benzyl)imidazo[1,2-c]pyrimidin-8-yl]acetic acid (14.2 mg, 73%) as slightly brown solid.

$^1$H-NMR (500 MHz, DMSO-d6): δ 3.82 (2H, s), 4.48 (2H, s), 7.38 (2H, d, J=8.5 Hz), 7.63 (1H, d, J=1.6 Hz), 7.72 (2H, d, J=8.5 Hz), 7.82 (1H, s), 7.91 (2H, d, J=8.2. Hz), 8.08 (1H, d, J=1.3 Hz), 8.12 (2H, d, J=7.9 Hz), 10.45 (1H, s), 12.48 (1H, br s)

Melting point: 205-207° C.

Molecular weight: 454.41

Mass spectrometry: 453 (M−H)−, 455 (M+H)+

In vitro activity grade: B

Diethyl 2-formylsuccinate

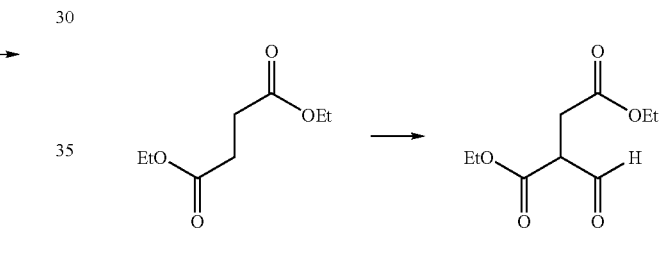

To a mixture of sodium (1.66 g, 72.13 mmol) in diethyl ether (35 mL) was added diethyl succinate (10 mL, 60.11 mmol) and ethyl formate (8.25 mL, 102.18 mmol) at room temperature, and the reaction mixture was refluxed for 5 hours. After the cooling to room temperature, water was added to the mixture until the sodium salt was dissolved completely and aqueous layer was separated. The aqueous layer was neutralized by 6M hydrochloric acid (10.8 mL) and extracted with diethyl ether. The extracts were washed with sat.NaHCO$_3$, dried over sodium sulfate, filtered and concentrated under reduced pressure. The crude product was purified by distillation (115-120° C., 10 mmHg) to give diethyl 2-formylsuccinate (6.55 g, 54%) as colorless oil.

Methyl [4-hydroxy-2-(4-nitrobenzyl)pyrimidin-5-yl]acetate

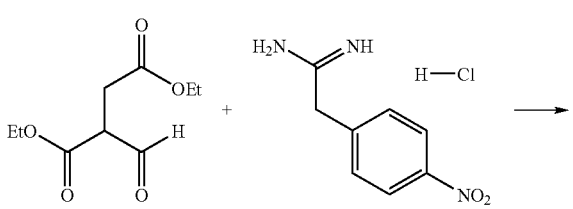

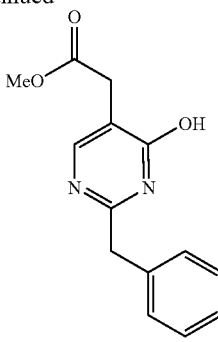

To a mixture of 2-(4-nitrophenyl)ethanimidamide hydrochloride (6.06 g, 28.12 mmol) and diethyl 2-formylsuccinate (6.54 g, 32.34 mmol) in methanol (100 mL) was added sodium methoxide (28% in methanol, 11.2 mL, 56.25 mmol) at room temperature, and the reaction mixture was stirred at 90° C. overnight. After the cooling to room temperature, the reaction was quenched with acetic acid (3.38 mL, 59.06 mmol) and water (100 mL) was added to. The resulting precipitates were collected by filtration and washed with water and acetone/diisopropyl ether (3/2) to give methyl [4-hydroxy-2-(4-nitrobenzyl)pyrimidin-5-yl]acetate (5.41 g, 64%) as brown solid.

Methyl [4-chloro-2-(4-nitrobenzyl)pyrimidin-5-yl]acetate

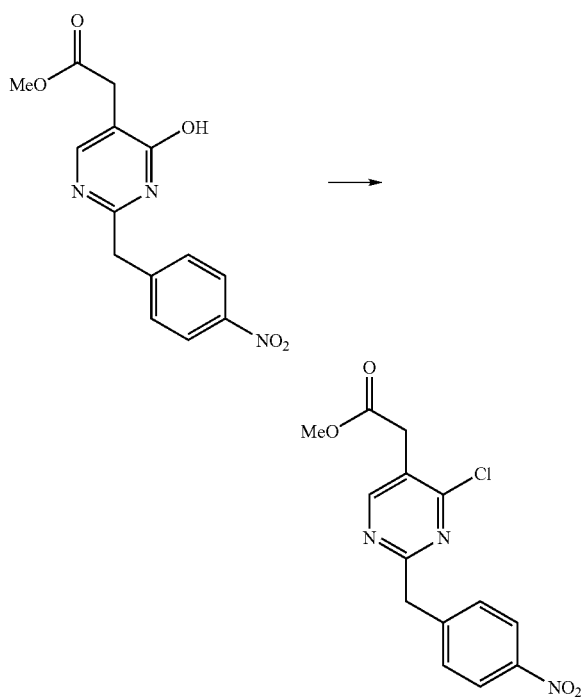

A mixture of methyl [4-hydroxy-2-(4-nitrobenzyl)pyrimidin-5-yl]acetate (4.0 g, 13.19 mmol), phosphorus oxychloride (6.15 mL, 65.95 mmol) and N,N-dimethylaniline (2.51 mL, 19.78 mmol) was stirred at 150° C. for 3 hours. After the removal of the excess phosphorus oxychloride, the residue was dissolved with ethyl acetate. The organic layer was washed with water and brine, dried over sodium sulfate, filtered and concentrated under reduced pressure. The crude product was purified by column chromatography on silica-gel, (hexane:ethyl acetate, 7/3) to give methyl [4-chloro-2-(4-nitrobenzyl)pyrimidin-5-yl]acetate (2.70 g, 64%) as orange solid.

Methyl [5-(4-nitrobenzyl)imidazo[1,2-c]pyrimidin-8-yl]acetate

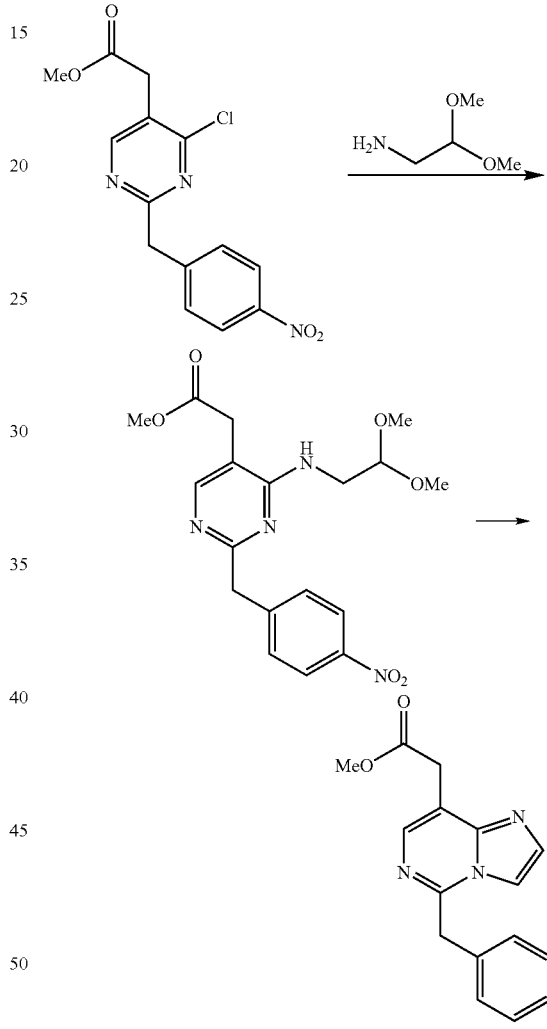

To a solution of methyl [4-chloro-2-(4-nitrobenzyl)pyrimidin-5-yl]acetate (2.70 g, 8.39 mmol) and aminoacetoaldehyde dimethyl acetal (1.83 mL, 16.78 mmol) in dioxane (40 mL) was added N,N-diisopropylethylamine (1.46 mL, 8.39 mmol). The mixture was stirred at 85° C. for 1 day. After cooling to room temperature, the reaction was quenched with water, and extracted with ethyl acetate. The extracts were washed with water and brine, dried over sodium sulfate, filtered and concentrated under reduced pressure. The crude product was purified by column chromatography on silica-gel, (ethyl acetate) to give methyl [4-[(2,2-dimethoxyethyl) amino]-2-(4-nitrobenzyl)-pyrimidin-5-yl]acetate (2.41 g, 74%) as brown oil.

A solution of methyl [4-[(2,2-dimethoxyethyl)amino]-2-(4-nitrobenzyl)pyrimidin-5-yl]acetate (1.00 g, 2.56 mmol) and HCl (1.0 M in water, 3.84 mL, 3.85 mmol) in dioxane (10 mL) was stirred at 85° C. for 1 hour. After the removal of the solvent in vacuo, water was added to the residue. The aqueous solution was neutralized by 1M NaOH and extracted with ethyl acetate. The extracts were washed with brine, dried over sodium sulfate, filtered and concentrated under reduced pressure. To the resulting crude product was added phosphorus oxychloride (1.4 mL) and the mixture was stirred at 85° C. for 3 hours. After the removal of the excess phosphorus oxychloride, the residue was dissolved with ethyl acetate. The organic layer was washed with water, sat.NaHCO$_3$ and brine, dried over sodium sulfate, filtered and concentrated under reduced pressure. The crude product was purified by column chromatography on silica-gel, (chloroform:methanol, 98/2) to give methyl [5-(4-nitrobenzyl)imidazo[1,2-c]pyrimidin-8-yl]acetate (28 mg, 3%) as brown oil.

Methyl (5-{4-[(3,4-dichlorobenzoyl)amino]benzyl}imidazo[1,2-c]pyrimidin-8-yl)acetate

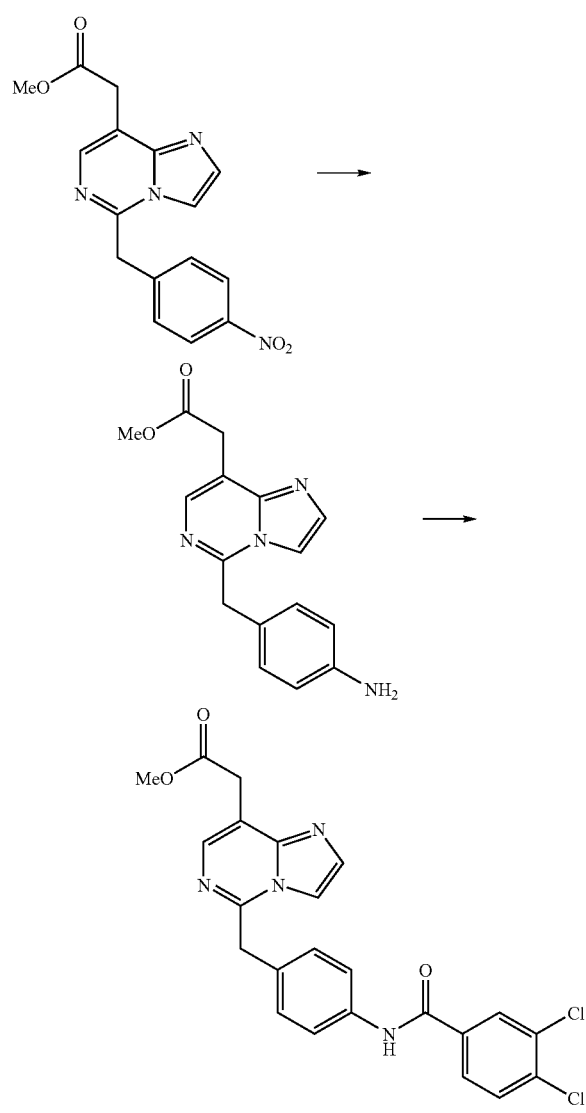

A mixture of methyl [5-(4-nitrobenzyl)imidazo[1,2-c]pyrimidin-8-yl]acetate (28 mg, 0.09 mmol) and Pd/C (wet, 3 mg) in methanol (1 mL) was stirred under hydrogen atmosphere for 1 hour. After the removal of Pd/C by filtration through a Celite pad, the filtrate was concentrated in vacuo. The resulting crude methyl [5-(4-aminobenzyl)imidazo[1,2-c]pyrimidin-8-yl]acetate (26 mg, 0.09 mmol) was dissolved with dichloromethane (1 mL). To this solution was added 3,4-dichloro-benzoic acid (20.1 mg, 0.11 mmol), 1-hydroxybenzotriazole (14.2 mg, 0.11 mmol), triethylamine (0.037 mL, 0.26 mmol) and 1-ethyl-3-(3-dimethylaminopropyl)carbodiimide hydrochloride (21.9 mg, 0.11 mmol) at room temperature. The mixture was stirred at room temperature overnight, and diluted with ethyl acetate. The solution was washed with water and brine, dried over sodium sulfate, filtered and concentrated under reduced pressure. The crude product was purified by preparative TLC (silica gel, chloroform:methanol, 19:1) to give methyl (5-{4-[(3,4-dichloro-benzoyl)amino]benzyl}imidazo[1,2-c]pyrimidin-8-yl)acetate (29 mg, 70%) as slightly yellow oil.

Example 2-2

(5-{4-[(3,4-Dichlorobenzoyl)amino]benzyl}imidazo[1,2-c]pyrimidin-8-yl)acetic acid

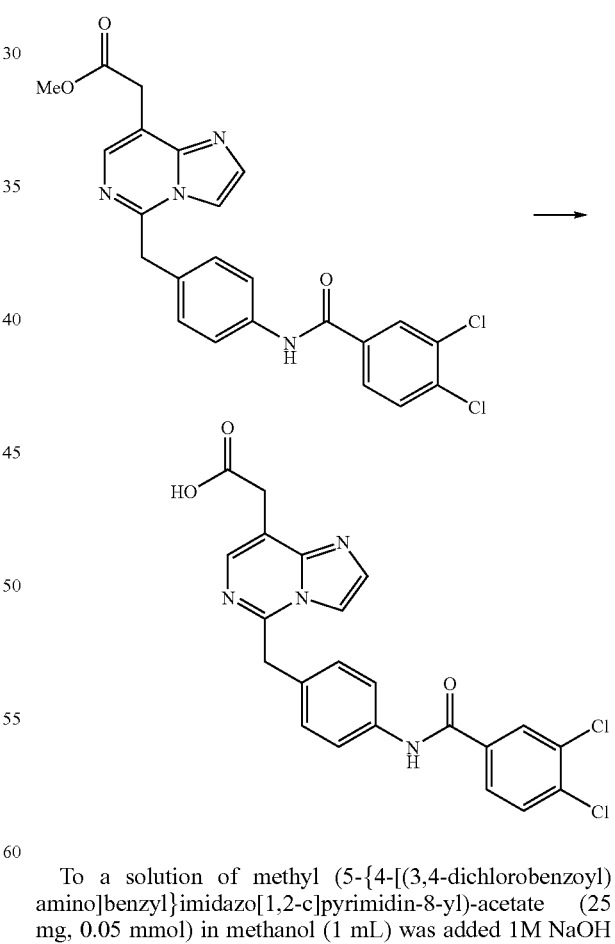

To a solution of methyl (5-{4-[(3,4-dichlorobenzoyl)amino]benzyl}imidazo[1,2-c]pyrimidin-8-yl)-acetate (25 mg, 0.05 mmol) in methanol (1 mL) was added 1M NaOH aqueous solution (0.2 mL) at room temperature, and the mixture was stirred for 1 hour. After the removal of methanol under reduced pressure, water was added to the residue. The solution was washed with diethyl ether and neutralized by aqueous hydrochloric acid. The resulting precipitates were collected by filtration and dried under reduced pressure to give (5-{4-[(3,4-dichlorobenzoyl)amino]benzyl}imidazo[1,2-c]pyrimidin-8-yl)acetic acid (17.2 mg, 71%) as slightly yellow solid.

$^1$H-NMR (500 MHz, DMSO-d6): δ 3.83 (2H, s), 4.48 (2H, s), 7.37 (2H, d, J=8.5 Hz), 7.63 (1H, d, J=1.3 Hz), 7.70 (2H, d, J=8.5 Hz), 7.81 (1H, d, J=8.5 Hz), 7.82 (1H, s), 7.92 (1H, dd, J=1.9, 8.5 Hz), 8.08 (1H, d, J=1.3 Hz), 8.19 (1H, d, J=2.2 Hz), 10.38 (1H, s), 12.47 (1H, br s)

Melting point: 185-188° C.
Molecular weight: 455.30
Mass spectrometry: 455 (M+H)+
In vitro activity grade: C

The invention claimed is:

1. A compound of the formula (I), its tautomeric or stereoisomeric form, or a salt thereof:

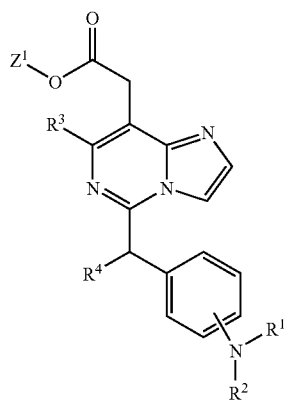

wherein
$Z^1$ represents hydrogen, $C_{1-6}$ alkyl, benzyl, 4-methoxybenzyl or 3,4-dimethoxybenzyl;
$R^1$ represents

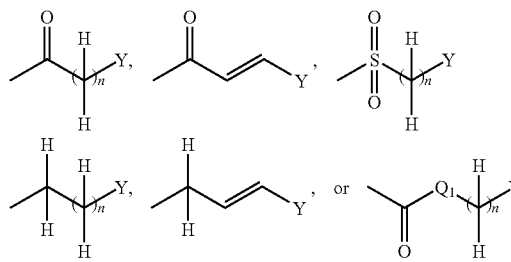

in which
n represents an integer of 0 to 6;
$Q_1$ represents —NH—, —N($C_{1-6}$ alkyl)-, or —O—;
Y represents hydrogen, $C_{3-8}$ cycloalkyl optionally substituted by $C_{1-6}$ alkyl, $C_{3-8}$ cycloalkyl fused by benzene, aryl or heteroaryl, wherein said aryl and heteroaryl are optionally substituted at a substitutable position with one or more substituents selected from the group consisting of cyano, halogen, nitro, guanidino, pyrrolyl, sulfamoyl, $C_{1-6}$ alkylaminosulfonyl, di($C_{1-6}$ alkyl)aminosulfonyl, phenyloxy, phenyl, amino, $C_{1-6}$ alkylamino, di($C_{1-6}$ alkyl)amino, $C_{1-6}$ alkoxycarbonyl, $C_{1-6}$ alkanoyl, $C_{1-6}$ alkanoylamino, carbamoyl, $C_{1-6}$ alkylcarbamoyl, di-($C_{1-6}$ alkyl)carbamoyl, $C_{1-6}$ alkylsulfonyl, $C_{1-6}$ alkyl optionally substituted by mono-, di-, or tri-halogen, $C_{1-6}$ alkoxy optionally substituted by mono-, di-, or tri-halogen and $C_{1-6}$ alkylthio optionally substituted by mono-, di-, or tri-halogen, or aryl fused by 1,3-dioxolane;
$R^2$ represents hydrogen or $C_{1-6}$ alkyl;
$R^3$ represents hydrogen, halogen, $C_{1-6}$ alkyl optionally substituted by mono-, di-, or tri-halogen, $C_{1-6}$ alkoxy optionally substituted by mono-, di-, or tri-halogen,

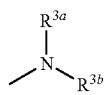

in which
$R^{3a}$ and $R^{3b}$ independently represent $C_{3-8}$ cycloalkyl, or $C_{1-6}$ alkyl optionally substituted by carboxy, $C_{3-8}$ cycloalkyl, carbamoyl, $C_{1-6}$ alkylcarbamoyl, aryl-substituted $C_{1-6}$ alkylcarbamoyl, $C_{1-6}$ alkylcarbamoyl, di($C_{1-6}$ alkyl)carbamoyl, $C_{3-8}$ cycloalkylcarbamoyl, $C_{3-8}$ heterocyclocarbonyl, $C_{1-6}$ alkylamino, di(C alkyl)amino or $C_{1-6}$ alkoxy,

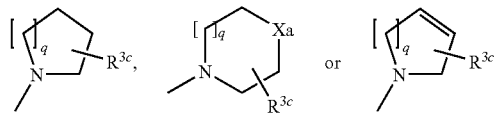

in which
q represents an integer of 1 to 3;
$R^{3c}$ represents hydrogen, hydroxy, carboxy, or $C_{1-6}$ alkyl optionally substituted by hydroxy, carboxy or (phenyl-substituted $C_{1-6}$ alkyl)carbamoyl;
Xa represents —O—, —S— or —N($R^{3d}$)—
in which
$R^{3d}$ represents hydrogen or $C_{1-6}$ alkyl; and
$R^4$ represents hydrogen or $C_{1-6}$ alkyl.

2. The compound of the formula (I), its tautomeric or stereoisomeric form, or a salt thereof as claimed in claim 1, wherein
$R^1$ represents

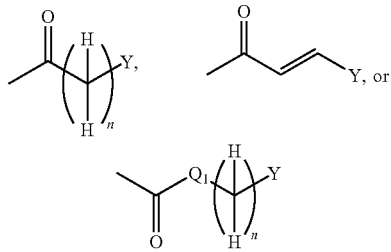

in which
n represents an integer of 0 to 2;
$Q_1$ represents —NH—, —N($C_{1-6}$ alkyl)-, or —O—;
Y represents $C_{3-8}$ cycloalkyl optionally substituted by $C_{1-6}$ alkyl, $C_{3-8}$ cycloalkyl fused by benzene, aryl selected from the group consisting of phenyl and naphthyl, or heteroaryl selected from the group consisting of indolyl, quinolyl, benzofuranyl, furanyl and pyridyl, wherein said aryl and heteroaryl are optionally substituted at a substitutable position with one or more substituents selected from the group consisting of cyano, halogen, nitro, pyrrolyl, sulfamoyl, $C_{1-6}$ alkylaminosulfonyl, di($C_{1-6}$ alkyl)aminosulfonyl, phenyloxy, phenyl, $C_{1-6}$alkylamino, di($C_{1-6}$ alkyl) amino, $C_{1-6}$ alkoxycarbonyl, $C_{1-6}$ alkanoylamino, carbamoyl, $C_{1-6}$ alkylcarbamoyl, di-($C_{1-6}$ alkyl)carbamoyl, $C_{1-6}$ alkylsulfonyl, $C_{1-6}$ alkyl optionally substituted by mono-, di-, or tri-halogen, $C_{1-6}$ alkoxy optionally substituted by mono-, di-, or tri-halogen and $C_{1-6}$ alkylthio optionally substituted by mono-, di-, or tri-halogen; and $R^2$ represents hydrogen.

3. The compound of the formula (I), its tautomeric or stereoisomeric form, or a salt thereof as claimed in claim 1, wherein $R^3$ represents hydrogen, halogen, $C_{1-6}$ alkyl optionally substituted by mono-, di-, or tri-halogen, $C_{1-6}$ alkoxy optionally substituted by mono-, di-, or tri-halogen,

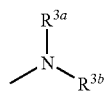

in which $R^{3a}$ and $R^{3b}$ independently represent $C_{1-6}$ alkyl optionally substituted by carboxy, $C_{3-8}$ cycloalkyl, carbamoyl, $C_{1-6}$ alkylcarbamoyl, di($C_{1-6}$ alkyl)carbamoyl, $C_{3-8}$ cycloalkylcarbamoyl, $C_{3-8}$ heterocyclocarbonyl, $C_{1-6}$ alkylamino, di($C_{1-6}$ alkyl)amino or $C_{1-6}$ alkoxy,

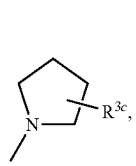 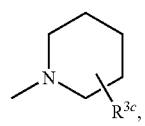 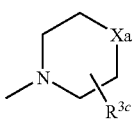 or

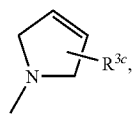

in which $R^{3c}$ represents hydrogen, hydroxy, carboxy, or $C_{1-6}$ alkyl optionally substituted by hydroxy, carboxy or (phenyl-substituted $C_{1-6}$ alkyl)carbamoyl;

Xa represents —O—, —S— or —N($R^{3d}$)—, in which $R^{3d}$ represents $C_{1-6}$ alkyl.

4. A compound of the formula (I-i), its tautomeric or stereoisomeric form, or a salt thereof;

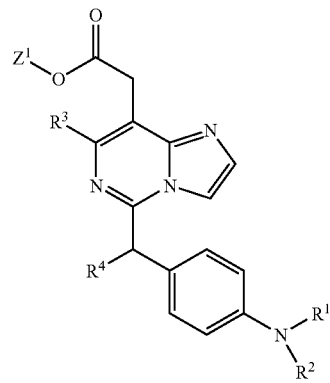

wherein $Z^1$ represents hydrogen, $C_{1-6}$ alkyl, benzyl, 4-methoxybenzyl or 3,4-dimethoxybenzyl;

$R^1$ represents

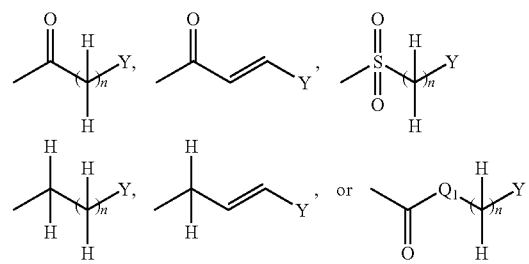

in which n represents an integer of 0 to 2;

$Q_1$ represents —NH—, —N($C_{1-6}$ alkyl)-, or —O—;

Y represents phenyl, naphthyl, indolyl, quinolyl, benzofuranyl, furanyl or pyridyl, wherein said phenyl, naphthyl, indolyl, quinolyl, benzofuranyl, furanyl and pyridyl are optionally substituted at a substitutable position with one or two substituents selected from the group consisting of cyano, halogen, nitro, phenyloxy, phenyl, $C_{1-6}$ alkyl optionally substituted by mono-, di-, or tri-halogen, $C_{1-6}$ alkoxy optionally substituted by mono-, di-, or tri-halogen and $C_{1-6}$ alkylthio optionally substituted by mono-, di-, or tri-halogen;

$R^2$ represents hydrogen or $C_{1-6}$ alkyl;

$R^3$ represents hydrogen, halogen, $C_{1-6}$ alkyl optionally substituted by mono-, di-, or tri-halogen, $C_{1-6}$ alkoxy,

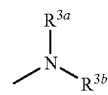

in which $R^{3a}$ and $R^{3b}$ independently represent $C_{3-8}$ cycloalkyl, or $C_{1-6}$ alkyl optionally substituted by $C_{3-8}$ cycloalkyl, carbamoyl, $C_{1-6}$ alkylcarbamoyl, (phenyl-substituted $C_{1-6}$ alkyl)carbamoyl, $C_{1-6}$ alkylcarbamoyl, di($C_{1-6}$ alkyl)carbamoyl, $C_{3-8}$ cycloalkylcarbamoyl, $C_{3-8}$ heterocyclocarbonyl, $C_{1-6}$ alkylamino, di($C_{1-6}$ alkyl)amino or $C_{1-6}$ alkoxy,

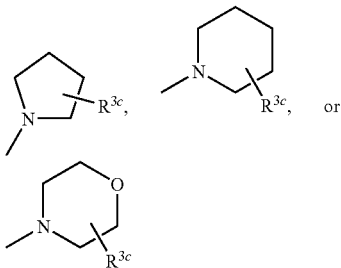

$R^{3c}$ represents hydrogen, hydroxy, carboxy, or $C_{1-6}$ alkyl optionally substituted by hydroxy, carboxy or (phenyl-substituted $C_{1-6}$ alkyl)carbamoyl; and
$R^4$ represents hydrogen or methyl.

5. The compound of the formula (I), its tautomeric or stereoisomeric form, or a salt thereof as claimed in claim 1, wherein said compound of the formula (I) is selected from the group consisting of:
[7-chloro-5-(4-{[4-(trifluoromethyl)benzoyl]amino}benzyl)imidazo[1,2-c]pyrimidin-8-yl]acetic acid;
(7-chloro-5-{4-[(3,4-dichlorobenzoyl)amino]benzyl}imidazo[1,2-c]pyrimidin-8-yl)acetic acid;
{7-chloro-5-[4-(2-naphthoylamino)benzyl]imidazo[1,2-c]pyrimidin-8-yl}acetic acid;
[7-chloro-5-(4-{[(2E)-3-phenylprop-2-enoyl]amino}benzyl)imidazo[1,2-c]pyrimidin-8-yl]acetic acid;
[7-chloro-5-(4-{[(2E)-3-(4-chlorophenyl)prop-2-enoyl]amino}benzyl)imidazo[1,2-c]pyrimidin-8-yl]acetic acid;
(5-{4-[(3,4-dichlorobenzoyl)amino]benzyl}imidazo[1,2-c]pyrimidin-8-yl)acetic acid; and
[5-(4-{[4-(trifluoromethyl)benzoyl]amino}benzyl)imidazo[1,2-c]pyrimidin-8-yl]acetic acid.

6. A pharmaceutical composition comprising a compound, its tautomeric or stereoisomeric form, or a physiologically acceptable salt thereof as claimed in claim 1 as an active ingredient, and one or more pharmaceutically acceptable excipients.

7. The pharmaceutical composition as claimed in claim 6, wherein the one or more pharmaceutically acceptable excipients is selected from carriers, diluents, flavoring agents, sweeteners, lubricants, solubilizers, suspending agents, binders, tablet disintegrating agents and encapsulating materials.

8. The pharmaceutical composition as claimed in claim 7, wherein the one or more pharmaceutically acceptable excipients is a carrier selected from lactose, starch, sucrose, glucose, sodium carbonate, mannitol, sorbitol, calcium carbonate, calcium phosphate, calcium sulfate and methyl cellulose.

9. The pharmaceutical composition as claimed in claim 8, further comprising a tablet disintegrating agent selected from maize, starch, methyl cellulose, agar bentonite, xanthan gum and alginic acid.

10. The pharmaceutical composition as claimed in claim 8, wherein the carrier is in a form selected from tablets, pills, powders, lozenges, elixirs, suspensions, emulsions, solutions, syrups, aerosols, ointments, soft and hard gelatin capsules, suppositories, sterile injectable solutions and sterile packaged powders.

11. The pharmaceutical composition as claimed in claim 7, wherein the one or more pharmaceutically acceptable excipients is a binder selected from gelatin, natural sugars, beta-lactose, corn sweeteners, natural and synthetic gums, acacia, tragacanth, sodium alginate, carboxymethylcellulose, polyethylene glycol and waxes.

12. The pharmaceutical composition as claimed in claim 7, wherein the one or more pharmaceutically acceptable excipients is a lubricant selected from magnesium stearate, sodium stearate, stearic acid, sodium oleate, sodium benzoate, sodium acetate, sodium chloride and talc.

13. The pharmaceutical composition as claimed in claim 6, wherein the amount of the active ingredient is from about 1 to about 99 weight percent, based on the total weight of the pharmaceutical composition.

* * * * *